(12) United States Patent
Dehottay et al.

(10) Patent No.: US 9,346,861 B2
(45) Date of Patent: May 24, 2016

(54) FERMENTATION PROCESS

(75) Inventors: Philippe Marc Helene Dehottay, Rixensart (BE); Philippe Goffin, Rixensart (BE)

(73) Assignee: GLAXOSMITHKLINE BIOLOGICALS S.A., Rixensart (BE)

( * ) Notice: Subject to any disclaimer, the term of this patent is extended or adjusted under 35 U.S.C. 154(b) by 0 days.

(21) Appl. No.: 14/111,223

(22) PCT Filed: Apr. 12, 2012

(86) PCT No.: PCT/EP2012/056728
§ 371 (c)(1),
(2), (4) Date: Oct. 11, 2013

(87) PCT Pub. No.: WO2012/140171
PCT Pub. Date: Oct. 18, 2012

(65) Prior Publication Data
US 2014/0050758 A1 Feb. 20, 2014

Related U.S. Application Data

(60) Provisional application No. 61/474,815, filed on Apr. 13, 2011.

(30) Foreign Application Priority Data

Apr. 13, 2011 (GB) .................................. 1106225.4

(51) Int. Cl.
*A61K 39/02* (2006.01)
*C12P 1/00* (2006.01)
*C12P 21/06* (2006.01)
*C07K 14/34* (2006.01)
*C07K 14/195* (2006.01)
*C12P 21/02* (2006.01)
*A61K 39/00* (2006.01)

(52) U.S. Cl.
CPC .............. *C07K 14/34* (2013.01); *C07K 14/195* (2013.01); *C12P 21/02* (2013.01); *A61K 2039/55544* (2013.01)

(58) Field of Classification Search
USPC .............. 424/93.2, 93.4, 184.1, 234.1, 236.1; 435/41, 69.1, 440
See application file for complete search history.

(56) References Cited

U.S. PATENT DOCUMENTS

| | | | |
|---|---|---|---|
| 4,356,170 A | 10/1982 | Jennings et al. | |
| 4,673,574 A | 6/1987 | Anderson | |
| 4,680,262 A | 7/1987 | Bochner et al. | |
| 4,709,107 A | 11/1987 | West et al. | |
| 5,601,827 A | 2/1997 | Collier et al. | |
| 5,846,711 A | 12/1998 | Moore et al. | |
| 5,917,017 A | 6/1999 | Collier et al. | |
| 8,426,168 B2 | 4/2013 | Stempfer et al. | |

FOREIGN PATENT DOCUMENTS

| | | |
|---|---|---|
| EP | 0161188 | 11/1985 |
| EP | 0208375 | 1/1987 |
| EP | 0477508 | 4/1992 |
| EP | 1762246 A1 | 3/2007 |
| WO | WO 90/10015 | 9/1990 |
| WO | WO 93/15760 | 8/1993 |
| WO | WO 95/08348 | 3/1995 |
| WO | WO 96/29094 | 9/1996 |
| WO | WO 98/42721 | 10/1998 |
| WO | WO 2011/042516 | 4/2011 |

OTHER PUBLICATIONS

Bethell, et al., "A novel method of activation of cross-linked agaroses with 1,1'-carbonyldiimidazole which gives a matrix for affinity chromatography devoid of additional charged groups", J. Biol. Chem., 254:2572-4 (1979).

Biogegrain, et al., "Release of periplasm proteins of *Brucella suis* upon acidic shock involve the outer membrane protein 0mp25", Infection and Immunity, 72(10):5693-5703, (2004).

Bishai, et al., "High-level expression of a proteolytically sensitive diphtheria toxin fragment in *Escherichi coli*", J. Bacteriol., 169:5140-5151 (1987).

Chen, et al., "A modified osmotic shock for periplasmic release of a recombinant creatinase from *Escherichia coli*", Biochem. Eng. J., 19:211-215 (2004).

Chu, et al., "Further studies on the immunogenicity of haemophilus influenzae Type b and pneumococcal type 6A polysaccharide-protein conjugates", Infect. Immunity, 40(1):245-256 (1983).

Hearn, et al., "Application of 1,1'-carbonyldiimidazole-activated matrices for the purification of proteins", J. Chromatogr., 218:509-18 (1981).

International Search Report, which issued on International Application No. PCT/EP2012/056728.

(Continued)

*Primary Examiner* — Rodney P Swartz
(74) *Attorney, Agent, or Firm* — Virginia G. Campen

(57) ABSTRACT

The present invention provides a process for periplasmic expression of a bacterial toxoid comprising the steps of:
a) growing a culture of a gram negative host cell in a fermentation medium, wherein the host cell is transformed with a polynucleotide, and wherein the polynucleotide encodes the bacterial toxoid and a periplasmic signal sequence; or providing a gram negative host cell wherein the host cell is transformed with a polynucleotide, the polynucleotide encodes the bacterial toxoid and a periplasmic signal sequence and wherein the gram negative host cell comprises the bacterial toxoid expressed in the periplasm;
a(i)) inducing expression of the bacterial toxoid;
b) maturing the host cell, wherein the maturing step comprises:
  I) subjecting the host cell to a pH shock;
  II) incubating the host cell with no feed addition; and/or
  III) subjecting the host cell to a temperature below −20° C.; and
c) extracting the bacterial toxoid from the host cell wherein the extraction process comprises osmotic shock.

16 Claims, 7 Drawing Sheets

(56) References Cited

OTHER PUBLICATIONS

O'Keefe, et al., "Cloned diphtheria toxin within the periplasm of *Escherichia-coli* causes lethal membrane damage at low PH", PNAS, 86(1): 343-346, (1989).

Rairakhwada, et al., "Gene cloning, characterization, and heterologous expression of levansucrase from Bacillus anyloliquefaciens", J. Ind. Microbiol. Biotechnol., 37:195-204 (2010).

Rathore, et al., "Optimization of an osmotic shock procedure for isolation of a protein product expressed in *E. coli*", Biotechnology Progress, 19(5):1541-1546, (2003).

Zabriskie, et al., "Effects of fermentation feeding strategies prior to induction of expression of a recombinant malaria antigen in *Escherichia coli*", J. Ind. Microbiol., 2:87-95 (1987).

Competty, B.: "Production of Human Paraoxonase I (huPONI) In *E. coli* with Periplasmic Expression and Chaperone Co-expression." Senior Honors Thesis. The Ohio State University, Mar. 2009, pp. 1-35.

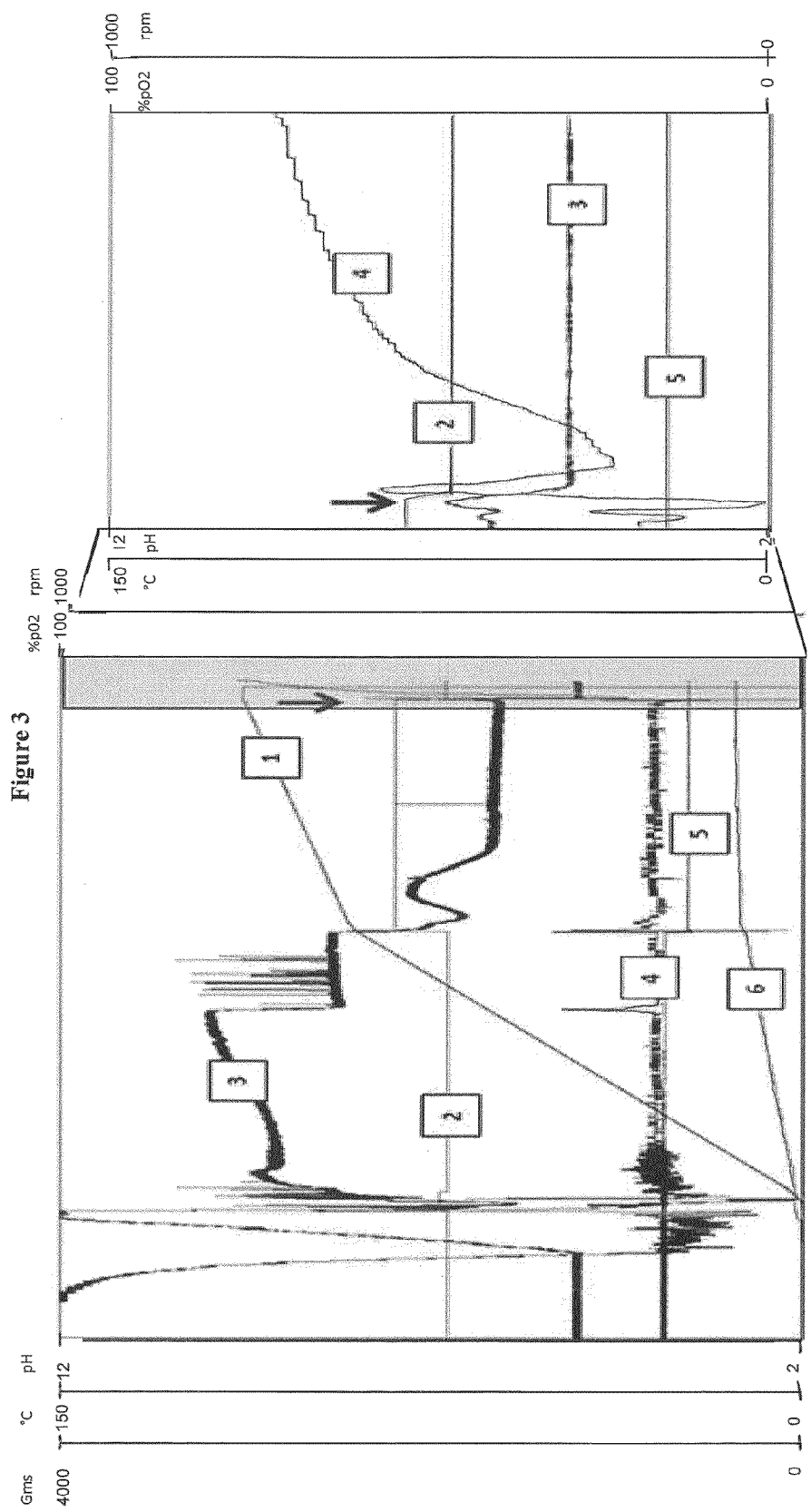

Figure 4A

SEQ ID NO 1: Nucleotide sequence of the PhtE signal sequence
ATGAAATTTAGTAAAAAATATATAGCAGCTGGATCAGCTGTTATCGTATCCTTGAGTCTATG
TGCCTATGCA

SEQ ID NO 2: Amino acid sequence of the PhtE signal sequence
MKFSKKYIAAGSAVIVSLSLCAYA

SEQ ID NO 3: Nucleotide sequence of the SipA signal sequence
ATGAAAATGAATAAAAAGGTACTATTGACATCGACAATGGCAGCTTCGCTATTATCA
GTCGCAAGTGTTCAAGCA

SEQ ID NO 4: Amino acid sequence of the SipA signal sequence
MKMNKKVLLTSTMAASLLSVASVQA

SEQ ID NO 5: Nucleotide sequence of the OmpA signal sequence
ATGAAAAAGACAGCTATCGCGATTGCAGTGGCACTGGCTGGTTTCGCTACCGTAGCG
CAGGCC

SEQ ID NO 6: Amino acid sequence of the OmpA signal sequence
MKKTAIAIAVALAGFATVAQA

SEQ ID NO 7: Nucleotide sequence of the NspA signal sequence
ATGAAAAAAGCACTTGCCACACTGATTGCCCTCGCTCTCCCGGCCGCCGCACTGGCG

SEQ ID NO 8: Amino acid sequence of the NspA signal sequence
MKKALATLIALALPAAALA

SEQ ID NO 9: Nucleotide sequence of the TorT signal sequence
ATGCGCGTACTGCTATTTTTACTTCTTTCCCTTTTCATGTTGCCGGCATTTTCG

SEQ ID NO 10: Amino acid sequence of the TorT signal sequence
MRVLLFLLLSLFMLPAFS

SEQ ID NO 11: Nucleotide sequence of the SfmC signal sequence
ATGATGACTAAAATAAAGTTATTGATGCTCATTATATTTTATTTAATCATTTCGGCC
AGCGCCCATGCT

Figure 4B

SEQ ID NO 13: Nucleotide sequence of the FocC signal sequence
ATGATGAAGCACATGCGTATATGGGCCGTTCTGGCATCATTTTTAGTCTTTTTTTAT
ATTCCGCAGAGCTATGCC

SEQ ID NO 14: Amino acid sequence of the FocC signal sequence
MMKHMRIWAVLASFLVFFYIPQSYA

SEQ ID NO 15: Nucleotide sequence of the CcmH signal sequence
ATGAGGTTTTTATTGGGCGTGCTGATGCTGATGATCTCCGGCTCAGCGCTGGCG

SEQ ID NO 16: Amino acid sequence of the CcmH signal sequence
MRFLLGVLMLMISGSALA

SEQ ID NO 17: Nucleotide sequence of the YraI signal sequence
ATGTCAAAACGAACATTCGCGGTGATATTAACCTTGTTGTGTAGCTTCTGTATTGGC
CAGGCGCTTGCA

SEQ ID NO 18: Amino acid sequence of the YraI signal sequence
MSKRTFAVILTLLCSFCIGQALA

SEQ ID NO 19: Nucleotide sequence of the TolB signal sequence
ATGATGAAGCAGGCATTACGAGTAGCATTTGGTTTTCTCATACTGTGGGCATCAGTT
CTGCATGCT

SEQ ID NO 20: Amino acid sequence of the TolB signal sequence
MMKQALRVAFGFLILWASVLHA

SEQ ID NO 21: nucleotide sequence of the NikA signal sequence
ATGCTCTCCACACTCCGCCGCACTCTATTTGCGCTGCTGGCTTGTGCGTCTTTTATC
GTCCATGCC

SEQ ID NO 22: Amino acid sequence of the NikA signal sequence
MLSTLRRTLFALLACASFIVHA

Figure 4C

SEQ ID NO 23: Nucleotide sequence of the FlgI signal sequence

ATGATTAAATTTCTCTCTGCATTAATTCTTCTACTGGTCACGACGGCGGCTCAGGCT

SEQ ID NO 24: Amino acid sequence of the FlgI signal sequence

MIKFLSALILLLVTTAAQA

SEQ ID NO 25: Nucleotide sequence of the DsbA signal sequence

ATGAAAAAGATTTGGCTGGCGCTGGCTGGTTTAGTTTTAGCGTTTAGCGCATCGGCG

SEQ ID NO 26: Amino acid sequence of the DsbA signal sequence

MKKIWLALAGLVLAFSASA

SEQ ID NO 27: Nucleotide sequence of the coding region of mature codon optimised CRM197

```
GGTGCGGATG ATGTGGTGGA TAGCAGCAAA TCTTTTGTGA TGGAAAACTT
TAGCAGCTAT CATGGCACCA AACCGGGCTA TGTGGATAGC ATTCAGAAAG
GCATCCAGAA ACCGAAAAGC GGCACCCAGG GCAACTATGA TGATGATTGG
AAAGAATTTT ATAGCACCGA TAACAAATAT GATGCGGCGG GTTATAGCGT
GGATAACGAA AATCCGCTGT CTGGCAAAGC GGGCGGTGTG GTGAAAGTGA
CCTATCCGGG CCTGACCAAA GTGCTGGCCC TGAAAGTGGA TAACGCGGAA
ACCATCAAAA AGAACTGGG CCTGAGCCTG ACCGAACCGC TGATGGAACA
GGTGGGCACC GAAGAATTTA TTAAACGCTT TGGCGATGGC GCGAGCCGTG
TGGTTCTGAG CCTGCCGTTT GCGGAAGGCA GCAGCAGCGT GGAATATATT
AACAACTGGG AACAGGCGAA AGCCCTGAGC GTGGAACTGG AAATTAACTT
TGAAACCCGT GGCAAACGTG GCCAGGATGC GATGTATGAA TACATGGCGC
AGGCGTGCGC GGGCAATCGT GTGCGTCGTA GCGTGGGCAG CAGCCTGAGC
TGCATTAACC TGGATTGGGA CGTCATTCGT GATAAAACCA AAACCAAAAT
CGAAAGCCTG AAAGAACATG GCCCGATCAA AAACAAAATG AGCGAAAGCC
CGAACAAAAC CGTGAGCGAA GAAAAGCGA AACAGTATCT GGAAGAATTT
CATCAGACCG CGCTGGAACA TCCGGAACTG AGCGAACTGA AAACCGTGAC
CGGCACCAAT CCGGTGTTTG CGGGTGCGAA CTATGCGGCG TGGGCGGTGA
ATGTGGCGCA GGTGATTGAT AGCGAAACCG CGGATAACCT GGAAAAAACC
ACCGCGGCCC TGAGCATTCT GCCGGGCATT GGCAGCGTGA TGGGCATTGC
```

Figure 4D

```
GGATGGCGCG GTGCATCATA ACACCGAAGA AATTGTGGCG CAGAGCATTG
CCCTGAGCAG CCTGATGGTG GCGCAGGCGA TTCCGCTGGT TGGCGAACTG
GTGGATATTG GCTTTGCGGC GTACAACTTT GTGGAAAGCA TCATCAACCT
GTTTCAGGTG GTGCATAACA GCTATAACCG TCCGGCGTAT TCTCCGGGTC
ATAAAACCCA GCCGTTTCTG CATGATGGCT ATGCGGTGAG CTGGAACACC
GTGGAAGATA GCATTATTCG TACCGGCTTT CAGGGCGAAA GCGGCCATGA
TATTAAAATT ACCGCGGAAA ACACCCCGCT GCCGATTGCG GGTGTTCTGC
TGCCGACCAT TCCGGGCAAA CTGGATGTGA ACAAAAGCAA AACCCATATT
AGCGTGAACG GTCGTAAAAT TCGTATGCGT TGCCGTGCGA TTGATGGCGA
TGTGACCTTT TGCCGTCCGA AAGCCCGGT GTATGTGGGC AACGGCGTGC
ACGCGAACCT GCATGTGGCG TTTCATCGTA GCAGCAGCGA AAAAATCCAT
AGCAACGAAA TTAGCAGCGA TAGCATTGGC GTGCTGGGCT ATCAGAAAAC
CGTGGACCAT ACCAAAGTGA ACTCTAAACT GAGCCTGTTC TTCGAAATCA
AAAGC
```

SEQ ID NO 28: Amino acid sequence of mature CRM197

```
GADDVVDSSK SFVMENFSSY HGTKPGYVDS IQKGIQKPKS GTQGNYDDDW
KEFYSTDNKY DAAGYSVDNE NPLSGKAGGV VKVTYPGLTK VLALKVDNAE
TIKKELGLSL TEPLMEQVGT EEFIKRFGDG ASRVVLSLPF AEGSSSVEYI
NNWEQAKALS VELEINFETR GKRGQDAMYE YMAQACAGNR VRRSVGSSLS
CINLDWDVIR DKTKTKIESL KEHGPIKNKM SESPNKTVSE EKAKQYLEEF
HQTALEHPEL SELKTVTGTN PVFAGANYAA WAVNVAQVID SETADNLEKT
TAALSILPGI GSVMGIADGA VHHNTEEIVA QSIALSSLMV AQAIPLVGEL
VDIGFAAYNF VESIINLFQV VHNSYNRPAY SPGHKTQPFL HDGYAVSWNT
VEDSIIRTGF QGESGHDIKI TAENTPLPIA GVLLPTIPGK LDVNKSKTHI
SVNGRKIRMR CRAIDGDVTF CRPKSPVYVG NGVHANLHVA FHRSSSEKIH
SNEISSDSIG VLGYQKTVDH TKVNSKLSLF FEIKS
```

FERMENTATION PROCESS

BACKGROUND

The present invention relates to a process for producing a recombinant protein, in particular a process for producing a recombinant protein comprising growing a host cell expressing the recombinant protein and a step of maturing the host cell. The invention also provides for a recombinant protein obtainable by the process of the invention and immunogenic compositions or vaccines comprising the recombinant protein.

Expression of certain toxins is known to be challenging, for example Diphtheria toxin. DT may be produced by purification of the toxin from a culture of *Corynebacterium diphtheriae* followed by chemical detoxification, or may be made by purification of a recombinant, or genetically detoxified analogue of the toxin (for example CRM197, or other mutants as described in U.S. Pat. No. 4,709,107, U.S. Pat. No. 5,846,711, U.S. Pat. No. 5,601,827, and U.S. Pat. No. 5,917,017).

Production of significant quantities of diphtheria toxins such as CRM197 for use in vaccines has been hindered due to low protein abundance. This problem has been addressed previously by expressing CRM197 in *E. coli* (Bishai et al., J. Bacteriology 169:5140-5151 (1987). Bishai et al. describe the expression of a recombinant fusion protein containing diphtheria toxin (including the tox signal sequence) this led to the production of degraded protein.

Cloning of Diphtheria fragments containing the tox signal sequence and expression of these sequences in *Escherichia coli* involves certain difficulties. The expressed protein is secreted into the periplasmic space and this secretion is associated with decreased viability of the host cells (O'Keefe et al., Proc. Natl. Acad. Sci., 86:343-346 (1989)) and increased proteolysis of the recombinant protein (Bishai et al., J. Bacteriology 169:5140-5151 (1987). For these reasons removal of the tox signal sequence so that expression is no longer periplasmic has been suggested, this can increase expression of Diphtheria toxoids (Bishai et al).

PCT/EP2010/065047 (WO 2011/042516) discloses, for the first time, successful periplasmic expression of CRM197. This increases the yield of CRM197, however even here improvements to the extraction process can be made to increase the yield. Rathore discloses the optimization of an osmotic shock procedure for isolation of a protein product expressed in *E. coli* (Rathore et al Biotechnol. Prog. 2003, 19, 1541-1546). Bochner et al also discloses a method for recovering periplasmic protein from a host cell (U.S. Pat. No. 4,680,262).

Thus the present invention provides an improved process for production of a recombinant polypeptide comprising a step of maturing the host cell, wherein this step may comprise any one or more of the following:
  (1) subjecting the host cell to a pH shock;
  (2) incubating the host cell; or
  (3) freezing the host cell.

This step of maturing the host cell has the surprising result of substantially increasing the efficiency of protein extraction.

BRIEF SUMMARY

In a first embodiment there is provided a process for periplasmic expression of a bacterial toxoid comprising the steps of:
  a) growing a culture of a gram negative host cell in a fermentation medium, wherein the host cell is transformed with a polynucleotide, and wherein the polynucleotide encodes the bacterial toxoid and a periplasmic signal sequence;
  a(i)) inducing expression of the bacterial toxoid;
  b) maturing the host cell, wherein the maturing step comprises:
    I) subjecting the host cell to a pH shock;
    II) incubating the host cell with no feed addition; and/or
    III) subjecting the host cell to a temperature below −20° C.; and
  c) extracting the bacterial toxoid from the host cell wherein the extraction process comprises osmotic shock.

In a second embodiment there is provided a process for periplasmic expression of a bacterial toxoid comprising the steps of:
  a) providing a gram negative host cell comprising the bacterial toxoid expressed in the periplasm;
  b) maturing the host cell, wherein the maturing step comprises:
    I) subjecting the host cell to a pH shock;
    II) incubating the host cell with no feed addition; and/or
    III) subjecting the host cell to a temperature below −20° C.; and
  c) extracting the bacterial toxoid from the host cell wherein the extraction process comprises osmotic shock.

In a third embodiment there is provided a bacterial toxoid obtainable by or obtained by the process of the invention.

In a fourth embodiment there is provided an immunogenic composition comprising the bacterial toxoid of the invention and a pharmaceutically acceptable excipient.

In a fifth embodiment there is provided a vaccine comprising the immunogenic composition of the invention.

In a sixth embodiment there is provided a use of the immunogenic composition or the vaccine of the invention in the manufacture of a medicament for the prevention or treatment of disease.

In a seventh embodiment there is provided a method of preventing or treating disease comprising administering the immunogenic composition or vaccine of the invention to a patient.

BRIEF DESCRIPTION OF THE DRAWINGS

FIG. 3—Depiction of a fermentation profile with the process parameters monitored during 20 liter scale fed-batch fermentation and maturation. Line 1 describes the amount of substrate added (grams), line 2 describes the pH, line 3 describes the stirring rate (rpm), line 4 describes the $pO_2$ (%), line 5 describes the temperature (° C.) and line 6 describes the amount of base added (grams). The arrow indicates the start of the maturation step. The maturation step is magnified in the right panel.

FIG. 4—sequence listings of polynucleotides and polypeptides of the invention.

DETAILED DESCRIPTION

Figure 1:
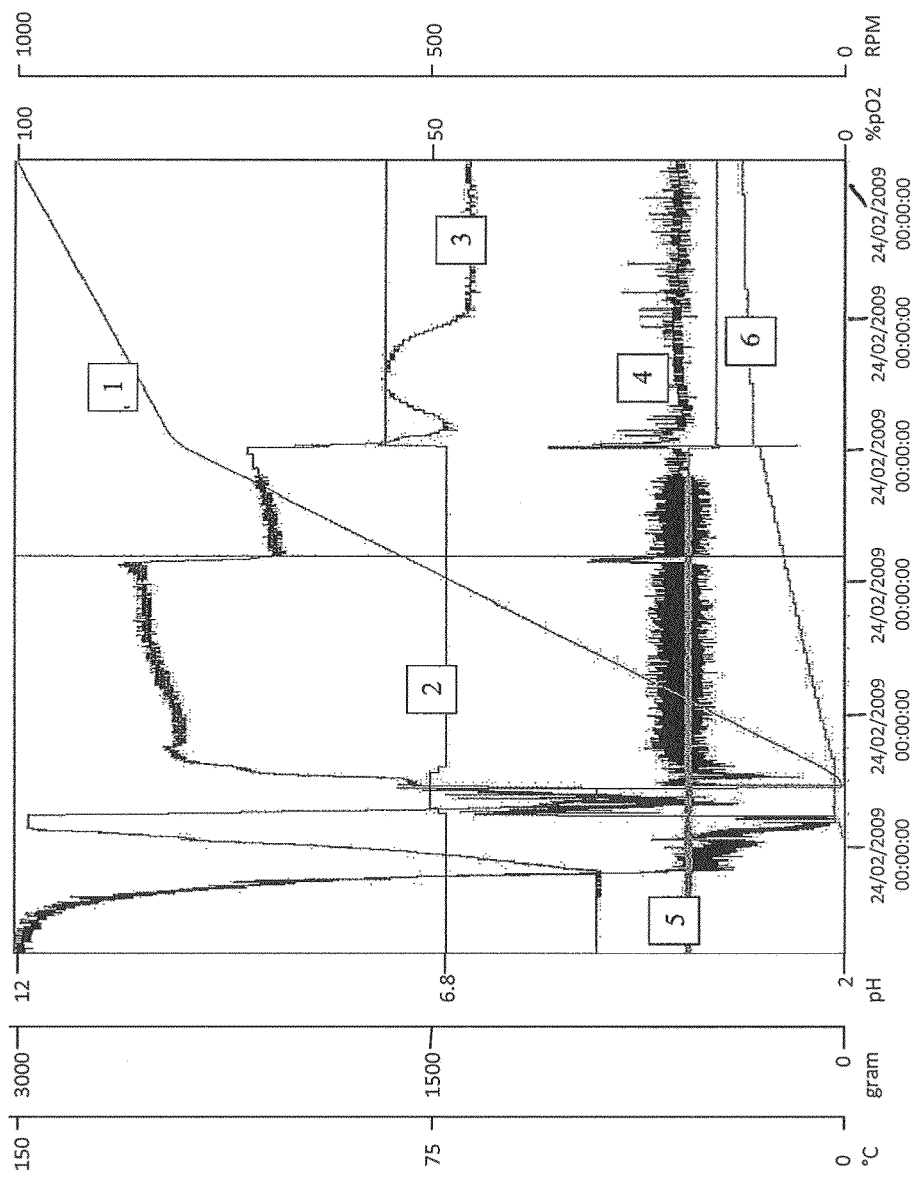
FIG. 1—Depiction of a fermentation profile with the process parameters monitored during 20 liter scale fed-batch fermentation. Line 1 describes the amount of substrate added (grams), line 2 describes the pH, line 3 describes the stirring rate (rpm), line 4 describes the $pO_2$ (%), line 5 describes the temperature (° C.) and line 6 describes the amount of base added (grams).

The present invention provides a process for periplasmic expression of a bacterial toxoid comprising the steps of:
- a) growing a culture of a gram negative host cell in a fermentation medium, wherein the host cell is transformed with a polynucleotide, and wherein the polynucleotide encodes the bacterial toxoid and a periplasmic signal sequence;
- a(i)) inducing expression of the bacterial toxoid;
- b) maturing the host cell, wherein the maturing step comprises:
  - I) subjecting the host cell to a pH shock;
  - II) incubating the host cell with no feed addition; and/or
  - III) subjecting the host cell to a temperature below −20° C.; and
- c) extracting the bacterial toxoid from the host cell wherein the extraction process comprises osmotic shock.

In a further embodiment there is provided a process for periplasmic expression of a bacterial toxoid comprising the steps of
- a) providing a gram negative host cell comprising the bacterial toxoid expressed in the periplasm;
- b) maturing the host cell, wherein the maturing step comprises:
  - I) subjecting the host cell to a pH shock;
  - II) incubating the host cell with no feed addition; and/or
  - III) subjecting the host cell to a temperature below −20° C.; and
- c) extracting the bacterial toxoid from the host cell wherein the extraction process comprises osmotic shock.

The periplasm is the space between the cytoplasmic membrane and the outer membrane in gram-negative bacteria. The term "periplasmic expression" refers to expression/production of a protein (such as the bacterial toxoid) within a host cell and its secretion into the periplasmic space of the host cell. Periplasmic expression is suitably achieved by using a signal sequence which is capable of directing an expressed protein to the periplasm. Typically at least 10, 20, 30, 40, 50, 60, 70, 80, 90 or 100% of the polypeptide of interest is directed to the periplasm when expressed in a gram negative bacterium with a periplasmic signal sequence.

A "recombinant" nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques. A "recombinant" protein is one that is encoded by a heterologous (e.g., recombinant) nucleic acid, which has been introduced into a host cell, such as a bacterial or eukaryotic cell. The nucleic acid can be introduced, on an expression vector having signals capable of expressing the protein encoded by the introduced nucleic acid or the nucleic acid can be integrated into the host cell chromosome.

The term 'maturing the host cell' refers to a process which is carried out prior to step c) and increases the efficiency with which a recombinant polypeptide such as the bacterial toxoid is released from the host cell or periplasm. The efficiency of release of the recombinant polypeptide from the periplasm may be determined in a number of ways. For example by measuring the amount of the recombinant polypeptide that is released from the periplasm after osmotic shock, and the amount of the recombinant polypeptide that remains cell-associated after this osmotic shock, this can be used to calculate the total amount of polypeptide of interest produced (cytoplasmic and periplasmic). The amount of polypeptide remaining cell associated after the osmotic shock can be determined by measuring the protein level after cell breakage using a French press. In order to calculate whether the efficiency with which the recombinant polypeptide is released from the periplasm has increased, the percentage of the polypeptide of interest which is released from the periplasm can be measured after carrying out the process with and without the maturation step, and the percentages compared.

Examples of steps which are capable of maturing the host cell are provided and include:
- (1) subjecting the host cell to a pH shock
- (2) incubating the host cell, optionally without feed addition, for at least 5 minutes, at least 10 minutes, at least 30 minutes, at least 1 hour or at least 2 hours at a temperature above 0° C., above 10° C. above 20° C. or above 23° C.
- (3) subjecting the host cell to a temperature below 0° C. for at least 1 hour, 2 hours, 5 hours, 12 hours, 24 hours, 1 day, 2 days or 5 days.

Step b) of the process for periplasmic expression of a bacterial toxoid may comprise any one of these steps, or two or three of these steps in combination.

The phrase 'extracting a recombinant protein from the host cell' refers to any process capable of releasing a recombinant protein (such as a bacterial toxoid) from the host cell, typically recombinant protein present in the periplasm. The phrase 'extracting the bacterial toxoid from the host cell' refers to any process capable of releasing a bacterial toxoid from the host cell, typically bacterial toxoid present in the periplasm. Such techniques are well known to the person skilled in the art and include for example osmotic shock or enzymatic methods. Optionally the enzymatic method comprises using lysozyme, zymolase or lysostaphin digestion.

The phrase 'periplasmic signal sequence' refers to a signal sequence which is capable of directing an expressed protein (such as a bacterial toxoid) to the periplasm, this may occur during translation (co-translational signal sequences) or after translation (post-translational signal sequences). A signal sequence is capable of directing an expressed protein to the periplasm if, when it is attached to a polypeptide of interest, during or after translation of the polypeptide in a gram negative bacteria, more of said polypeptide is found in the periplasm of a gram negative bacteria than in the absence of the signal sequence. In an embodiment at least 50, 60, 70, 80, 90 or 100% of the polypeptide of interest is directed to the periplasm when expressed in a gram negative bacterium such as *E. coli*. An assay to test whether a signal sequence is capable of directing periplasmic expression can be carried out using reporter proteins. For example a periplasmic signal sequence can be inserted upstream of a gene encoding green fluorescent protein, this protein can be expressed in a host cell of the invention. A microscope can be used to judge the comparative levels of the green fluorescent protein in the cytoplasm and the periplasm. In some embodiments the recombinant protein may be secreted.

The polynucleotide encodes a periplasmic signal sequence operably linked to a sequence encoding a recombinant protein (such as the bacterial toxoid).

In one embodiment the process further comprises a step a(i)) of inducing expression of a recombinant protein (such as the bacterial toxoid). The term 'inducing expression of the protein' refers to a process of adding an inducing agent such as IPTG (isopropyl β-D-1-thiogalactopyranoside) to the culture, or modifying the temperature of the culture, causing expression of polypeptide at an increased rate. The term 'inducing expression of the protein' further encompasses incubating the culture under suitable conditions to allow expression to take place for a certain period of time before the next step of the process. The entire period of time taken to both initiate expression (by addition of inducing agent or change in temperature) and to allow expression to take place (incubation under suitable conditions) is referred to herein as the "induction phase". According to one embodiment of the invention, the induction phase may last from 5 minutes to 72 hours, from 30 minutes to 48 hours, from 1 to 36 hours, from 6 to 26 hours or for 12 to 24 hours, for example approximately 6, 12, 18, 24, 26, 36, 48 or 72 hours. According to one aspect of the invention, step a(i)) of inducing expression of the recombinant protein takes place after step a) and before step b), and is hereinafter referred to as step a(i)).

In one embodiment step b) comprises subjecting the host cell to a pH shock. For the purposes of the invention the phrase 'subjecting the host cell to a pH shock' refers to increasing or decreasing the pH of the fermentation medium. The pH shock can be performed on host cells in the fermenter, alternatively the pH shock can be performed on host cells that have been concentrated by, for example, centrifugation. The pH shock can be performed by adding acid or base to the solution in which the host cell is suspended.

In one embodiment the pH shock comprises changing the pH of the fermentation medium by more than 0.2 pH units, more than 0.3 pH units, more than 0.4 pH units, more than 0.5 pH units or more than 0.6 pH units. In general 'changing the pH of the fermentation medium' comprises increasing or decreasing the pH of the fermentation medium and this can be performed by adding components to the fermentation medium, e.g. adding an acid or a base to the fermentation medium.

In one embodiment the pH shock comprises increasing the pH of the fermentation medium by more than 0.2 pH units, more than 0.3 pH units, more than 0.4 pH units, more than 0.5 pH units or more than 0.6 pH units. This can be performed e.g. by adding an alkalinising agent such as a base to the fermentation medium.

In one embodiment the pH shock comprises decreasing the pH of the fermentation medium by more than 0.2 pH units, more than 0.3 pH units, more than 0.4 pH units, more than 0.5 pH units or more than 0.6 pH units. This can be performed e.g. by adding an acidifying agent such as an acid to the fermentation medium.

In a further embodiment the pH shock comprises changing the pH of the fermentation medium by between 0.1 and 2.0 pH units, between 0.1 and 2.0 pH units, between 0.1 and 1.5 pH units, between 0.2 and 2.0 pH units, between 0.2 and 1.5 pH units, between 0.2 and 1.0 pH units, between 0.5 and 2.0 pH units, between 0.5 and 1.5 pH units, between 0.5 and 2.0 pH units or between 0.7 and 1.5 pH units.

In a further embodiment the pH shock comprises increasing the pH of the fermentation medium by between 0.1 and 2.0 pH units, between 0.1 and 2.0 pH units, between 0.1 and 1.5 pH units, between 0.2 and 2.0 pH units, between 0.2 and 1.5 pH units, between 0.2 and 1.0 pH units, between 0.5 and 2.0 pH units, between 0.5 and 1.5 pH units, between 0.5 and 2.0 pH units or between 0.7 and 1.5 pH units.

In a further embodiment the pH shock comprises decreasing the pH of the fermentation medium by between 0.1 and 2.0 pH units, between 0.1 and 2.0 pH units, between 0.1 and 1.5 pH units, between 0.2 and 2.0 pH units, between 0.2 and 1.5 pH units, between 0.2 and 1.0 pH units, between 0.5 and 2.0 pH units, between 0.5 and 1.5 pH units, between 0.5 and 2.0 pH units or between 0.7 and 1.5 pH units.

In one embodiment the pH shock is achieved by addition of a base. In one embodiment the base is selected from the group consisting of sodium hydroxide, ammonium hydroxide, sodium carbonate, sodium phosphate, and sodium bicarbonate. In a further embodiment the base is ammonium hydroxide ($NH_4OH$) or sodium hydroxide (NaOH). In a further embodiment the base is ammonium hydroxide. In a further embodiment the base is sodium hydroxide.

In one embodiment the pH shock is achieved by addition of an acid. In one embodiment the acid is selected from the group consisting of hydrochloric acid, sulphuric acid, carbonic acid, phosphoric acid, acetic acid and lactic acid. In one embodiment the acid is phosphoric acid ($H_3PO_4$).

In one embodiment step b) comprises an incubation step wherein the incubation step comprises incubating the host cell for at least 5 minutes, at least 10 minutes, at least 30 minutes, at least 1 hour or at least 2 hours at a temperature above 0° C., above 5° C., above 10° C., above 15° C., above 20° C. or above 23° C. In one embodiment the incubation step comprises incubating the host cell at a temperature between 10° C.-50° C., 15° C.-45° C., 20° C.-40° C., 22° C.-38° C., 15° C.-50° C., 15° C.-40° C., 20° C.-38° C., 20° C.-50° C. 22° C.-50° C., 22° C.-45° C. 22° C.-40° C., 23° C.-50° C., 23° C.-45° C., 23° C.-40° C., 23° C.-38° C., 23° C.-30° C., 25° C.-0.50° C., 25° C.-45° C., 25° C.-40° C., 25° C.-38° C., 25° C.-30° C.

In one embodiment the incubation step comprises incubating the host cell at a temperature around 23° C. or around 37° C.

In one embodiment the incubation step comprises incubating the host cell for at least 5 minutes, at least 7 minutes, at least 10 minutes, at least 15 minutes, at least 30 minutes, at least 1 hour, at least 90 minutes, at least 2 hours, at least 3 hours, at least 5 hours, at least 24 hours or at least 2 days. In a further embodiment the incubation step comprises incubating the host cell for between 5 minutes and two years, between 5 minutes and one year, between 5 minutes and 6 months, between 5 minutes and 3 months, between 5 minutes and one month, between 5 minutes and 2 weeks, between 5 minutes and one week, between 5 minutes and 24 hours, between 5 minutes and 12 hours, between 5 minutes and 6 hours, between 5 minutes and 3 hours, between 5 minutes and 2 hours, between 5 minutes and 1 hour, between 5 minutes and 30 minutes between 5 minutes and 15 minutes, between 10 minutes and one year, between 10 minutes and 6 months, between 10 minutes and 3 months, between 10 minutes and one month, between 10 minutes and 2 weeks, between 10 minutes and one week, between 10 minutes and 24 hours, between 10 minutes and 12 hours, between 10 minutes and 6 hours, between 10 minutes and 3 hours, between 10 minutes and 2 hours, between 10 minutes and 1 hour, between 10 minutes and 30 minutes between 10 minutes and 15 minutes, between 30 minutes and one year, between 30 minutes and 6 months, between 30 minutes and 3 months, between 30 minutes and one month, between 30 minutes and 2 weeks, between 30 minutes and one week, between 30 minutes and 24 hours, between 30 minutes and 12 hours, between 30 minutes and 6 hours, between 30 minutes and 3 hours, between 30 minutes and 2 hours, between 30 minutes and 1 hour, between 1 hour and one year, between 1 hour and 6 months, between 1 hour and 3 months, between 1 hour and one month, between 1 hour and 2 weeks, between 1 hour and one week, between 1 hour and 24 hours, between 1 hour and 12 hours, between 1 hour and 6 hours, between 1 hour and 3 hours or between 1 hour and 2 hours.

In one embodiment the feed rate during the incubation step is lower than the feed rate during step a). The feed rate (or substrate provision rate) is the rate of substrate addition (ml $min^{-1}$) wherein the substrate comprises the food source for the cultured host cell. In one embodiment the feed rate during the incubation step is less than 75%, 50%, 35%, 25%, 15%, 10%, 5%, 4%, 3%, 2% or 1% of the feed rate used in step a). In a further embodiment there is no feed addition during the incubation step, in general this means that no substrate is added during the incubation step.

In one embodiment the pH of the culture medium is allowed to fluctuate during the incubation step. In one embodiment the pH alters by around 0.1 units. In a further embodiment there is no pH control during the incubation step. This means that no further acid or base is added during the incubation step in order to maintain a constant pH.

In a further embodiment step b) comprises subjecting the host cell to a temperature below 0° C. for at least 30 minutes, 1 hour, 2 hours, 5 hours, 12 hours, 24 hours, 1 day, 3 days, 4 days, 5 days, 15 days, 1 month, 6 months, 12 months, 1 year or 2 years. In one embodiment the host cell is subjected to a temperature below 0° C., −5° C., −10° C., −20° C., −40° C., −60° C., −70° C. or −80° C. In a further embodiment, the host cell is subjected to a temperature of from 0 to −100° C., from 0 to −80° C., from 0 to −20° C., from 0 to −18° C., from −5 to −80° C., from −10 to −80° C., from −20 to −80° C., or from −25 to −80° C. for example a temperature of approximately 0° C., −5° C., −10° C., −15° C., −18° C., −22° C., −25° C., −30° C., −40° C., −50° C., −60° C., −70° C. or −80° C. In one embodiment the host cell is subjected to a temperature below 0° C. for between 5 minutes and 10 years, 15 minutes and 10 years, 40 minutes and 10 years, 1 hour and 10 years, 15 minutes and 5 years, 30 minutes and 5 years, 1 hour and 5 years, 15 minutes and 3 years, 30 minutes and 3 years, 1 hour and 3 years, 15 minutes and 2 years, 30 minutes and 2 years, 1 hour and 2 years, 15 minutes and 1 year, 30 minutes and 1 year, 1 hour and 1 year, 1 hour and 15 days, 2 hours and 10 days, 12 hours and 7 days or 2 and 5 days, for example approximately 30 minutes, 1 hour, 2 hours, 5 hours, 12 hours, 1 day, 2 days, 3 days, 4 days, 5 days, 6 days, 7 days, 10 days, 15 days, 1 month, 6 months or 12 months.

In a further embodiment step b) comprises freezing the host cell for at least 30 minutes, 1 hour, 2 hours, 3 hours, 5 hours, 12 hours, 24 hours, 1 day, 2 days, 5 days 15 days, 1 month, 3 months, 6 months, 1 year, 2 years, 5 years or 10 years. In a further embodiment step b) comprises freezing the host cell for between 5 minutes and 10 years, between 5 minutes and 5 years, between 5 minutes and 2 years, between 30 minutes and 10 years, between 30 minutes and 5 years, between 30 minutes and 2 years, between 1 hour and 10 years, between 1 hour and 5 years or between 1 hour and 2 years. The term 'freezing' refers to exposing the host cell to a temperature below 0° C. In a further embodiment step c) comprises freezing the host cell at a temperature below 0° C., −5° C., −10° C., −20° C., −30° C., −40° C., −50° C., −70° C. or −80° C. Freezing the host cell may result in the production of ice crystals, however lowering the temperature of the host cell below 0° C. without resulting in the production of ice crystals is also considered to be 'freezing the host cell'.

In one embodiment step b) further comprises thawing the cells. The term 'thawing the cells' refers to raising the temperature of the host cell above 0° C., 10° C. or 20° C. In general 'thawing the cells' will occur after the cells have been frozen but before step c).

In one embodiment step b) comprises subjecting the host cell to a pH shock followed by an incubation step wherein the incubation step comprises incubating the host cell for at least 5 minutes, at least 10 minutes, at least 30 minutes, at least 1 hour or at least 2 hours at a temperature above 0° C., above 10° C. or above 20° C.

In a further embodiment step b) comprises an incubation step wherein the incubation step comprises incubating the host cell for at least 5 minutes, at least 10 minutes, at least 30 minutes, at least 1 hour or at least 2 hours at a temperature above 0° C., above 10° C. or above 20° C., followed by subjecting the host cell to a pH shock.

In a further embodiment step b) comprises an incubation step wherein the incubation step comprises incubating the host cell for at least 5 minutes, at least 10 minutes, at least 30 minutes, at least 1 hour or at least 2 hours at a temperature above 0° C., above 10° C. or above 20° C. followed by freezing the host cell for at least 1 hour, 2 hours, 5 hours, 12 hours, 24 hours, 1 day, 2 days or 4 days.

In a further embodiment step b) comprises subjecting the host cell to pH shock followed by freezing the host cell for at least 1 hour, 2 hours, 5 hours, 12 hours, 24 hours, 1 day, 2 days or 4 days.

In a further embodiment step b) comprises subjecting the host cell to a pH shock followed by an incubation step wherein the incubation step comprises incubating the host cell for at least 5 minutes, at least 10 minutes, at least 30 minutes, at least 1 hour or at least 2 hours at a temperature above 0° C., above 10° C. or above 20° C. followed by freezing the host cell for at least 1 hour, 2 hours, 5 hours, 12 hours, 24 hours, 1 day, 2 days or 4 days.

In a further embodiment step b) comprises an incubation step wherein the incubation step comprises incubating the host cell for at least 5 minutes, at least 10 minutes, at least 30 minutes, at least 1 hour or at least 2 hours at a temperature above 0° C., above 10° C. or above 20° C., followed by subjecting the host cell to a pH shock followed by freezing the host cell for at least 1 hour, 2 hours, 5 hours, 12 hours, 24 hours, 1 day, 2 days or 4 days.

Step b) may be performed directly on the cells within the whole broth (the product of step a) and/or step a)(i)), alternatively cells may be removed from the fermentor prior to step b), in a further embodiment the cells are removed from the fermenter and concentrated for example using centrifugation prior to step b).

In one embodiment the host cell is a gram negative host cell, e.g. a gram negative bacterium. In a further embodiment the gram negative host cell is selected from the group consisting of *E. coli, Acinetobacter, Actinobacillus, Bordetella, Brucella, Campylobacter, Cyanobacteria, Enterobacter, Erwinia, Franciscella, Helicobacter, Hemophilus, Klebsiella, Legionella, Moraxella, Neisseria, Pasteurella, Pseudomonas, Proteus, Salmonella, Serratia, Shigella, Treponema, Vibrio*, and *Yersinia*. In a further embodiment the gram negative host cell is selected from the group consisting of *E. coli. Pseudomonas*, and *Moraxella*. In a further embodiment the gram negative host cell is *E. coli*.

In one embodiment step c) comprises osmotic shock.

In one embodiment the cells are not killed prior to step b). In a further embodiment step b) is performed on live host cells. A host cell is considered to be 'live' if the majority of the cells within the culture of the host cell are capable of replication. Examples of processes that are known to 'kill' cells include exposure of the host cell to alcohol or to high temperatures. In one embodiment the host cell is not subjected to temperatures above 40° C., above 50° C. or above 60° C. prior to step b). In a further embodiment an alcohol is not added to the culture of the host cell prior to step b). The term 'alive during step b)' means that the majority of cells within the culture of the host cell are alive for the entire duration of the maturing step b) or a substantial portion thereof.

In one embodiment the recombinant protein is a bacterial, viral or cancer antigen. In one embodiment the recombinant protein is a prokaryotic protein. In one embodiment the recombinant protein is not a growth hormone. In one embodiment the recombinant protein is not human growth hormone. In one embodiment the recombinant protein is not CRM197. In one embodiment the recombinant protein is not CRM 197 and the periplasmic signal sequence is not flgI. In one embodiment the recombinant protein is a soluble protein. In a further embodiment the recombinant protein is a surface associated protein. In a further embodiment the recombinant protein is a toxoid, for example a bacterial toxoid. In a further embodiment the recombinant protein is a protein derived from *C. diphtheriae, S. pneumoniae, H. influenzae, Moraxella, N. meningitidis, S. aureus, E. faecalis, E. faecium, Salmonella, C. trachomatis,* or *S. epidermidis*. In a further embodiment the recombinant protein is CRM197.

In one embodiment the periplasmic signal sequence is a heterologous signal sequence.

The term "heterologous" refers to two components, e.g. polypeptide or polynucleotide sequences, from two different sources. For example, a heterologous protein is one that is encoded by a polynucleotide or nucleic acid derived from different sources, comprising artificial combination of polynucleotide or nucleic acids sequences from different sources, or one which is not native to the cell type in which it is expressed. For example this refers to a signal sequence which is not normally associated with the recombinant protein, for example a signal sequence which, in its native state, directs a different protein to the periplasm. For example, flgI directs the flgI protein to the periplasm in its native state, so can be considered a heterologous signal sequence if it directs a protein other than flgI to the periplasm.

In one embodiment the periplasmic signal sequence comprises
 a) any one of SEQ ID NO: 2, 4, 6, 8, 10, 12, 14, 18, 20, 22, 24, or 26;
 b) variants of SEQ ID NO: 2, 4, 6, 8, 10, 12, 14, 18, 20, 22, 24, or 26 containing 1, 2, or 3 point mutations, insertions or deletions; or
 c) fragments of at least 10 amino acids of SEQ ID NO: 2, 4, 6, 8, 10, 12, 14, 18, 20, 22, 24, or 26.

Optionally the periplasmic signal sequence comprises any one of SEQ ID NO: 2, 4, 6, 8, 10, 12, 14, 16, 18, 20, 22, 24, or 26, or any one of SEQ ID NO: 2, 4, 10, 12, 14, 16, 18, 20, 22, 24, or 26, or any one of SEQ ID NO: 2, 4, 10, 12, 14, 16, 18, 20, 22, or 24, or SEQ ID NO: 24 or any one of SEQ ID NO: 2, 4, or 24, or any one of SEQ ID NO: 2, 10, or 24, or any one of SEQ ID NO: 2, 12, or 24, or any one of SEQ ID NO: 2, 14, or 24, or any one of SEQ ID NO: 4, 10 or 24, or any one of SEQ ID NO: 4, 12, or 24, or any one of SEQ ID NO: 4, 16, or 24, or any one of SEQ ID NO: 4, 18 or 24, or any one of SEQ ID NO: 4, 20 or 24, or any one of SEQ ID NO: 4, 22, or 24, or any one of SEQ ID NO: 10, 12, or 24, or any one of SEQ ID NO: 10, 14, or 24, or any one of SEQ ID NO: 10, 16, or 24, or any one of SEQ ID NO: 10, 18, or 24, or any one of SEQ ID NO: 10, 22 or 24, or any one of SEQ ID NO: 12, 14, or 24, or any one of SEQ ID NO: 12, 16, or 24, or any one of SEQ ID NO: 12, 18, or 24, or any one of SEQ ID NO: 12, 20, or 24, or any one of SEQ ID NO: 12, 22, or 24, or any one of SEQ ID NO: 14, 16, or 24, or any one of SEQ ID NO: 14, 18, or 24, or any one of SEQ ID NO: 14, 20 or 24, or any one of SEQ ID NO: 14, 22, or 24, or any one of SEQ ID NO: 16, 18, or 24, or any one of SEQ ID NO: 16, 20 or 24, or any one of SEQ ID NO: 16, 22, or 24, or any one of SEQ ID NO: 18, 20 or 24, or any one of SEQ ID NO 18, 22, or 24.

In a further embodiment the periplasmic signal sequence comprises fragments of at least 10, 12, 15, 18 or 20 amino acids of any one of SEQ ID NO: 2, 4, 6, 8, 10, 12, 14, 16, 18, 20, 22, 24, or 26 or any one of SEQ ID NO: 2, 4, 10, 12, 14, 16, 18, 20, 22, 24, or 26, or any one of SEQ ID NO: 2, 4, 10, 12, 14, 16, 18, 20, 22, or 24, or SEQ ID NO: 24, or any one of SEQ ID NO: 2, 4, or 24, or any one of SEQ ID NO: 2, 10, or 24, or any one of SEQ ID NO: 2, 12, or 24, or any one of SEQ ID NO: 2, 14, or 24, or any one of SEQ ID NO: 4, 10 or 24, or any one of SEQ ID NO: 4, 12, or 24, or any one of SEQ ID NO: 4, 16, or 24, or any one of SEQ ID NO: 4, 18 or 24, or any one of SEQ ID NO: 4, 20 or 24, or any one of SEQ ID NO: 4, 22, or 24, or any one of SEQ ID NO: 10, 12, or 24, or any one of SEQ ID NO: 10, 14, or 24, or any one of SEQ ID NO: 10, 16, or 24, or any one of SEQ ID NO: 10, 18, or 24, or any one of SEQ ID NO: 10, 22 or 24, or any one of SEQ ID NO: 12, 14, or 24, or any one of SEQ ID NO: 12, 16, or 24, or any one of SEQ ID NO: 12, 18, or 24, or any one of SEQ ID NO: 12, 20, or 24, or any one of SEQ ID NO: 12, 22, or 24, or any one of SEQ ID NO: 14, 16, or 24, or any one of SEQ ID NO: 14, 18, or 24, or any one of SEQ ID NO: 14, 20 or 24, or any one of SEQ ID NO: 14, 22, or 24, or any one of SEQ ID NO: 16, 18, or 24, or any one of SEQ ID NO: 16, 20 or 24, or any one of SEQ ID NO: 16, 22, or 24, or any one of SEQ ID NO: 18, 20 or 24, or any one of SEQ ID NO 18, 22, or 24 which are capable of directing transport of a protein to the bacterial periplasm.

In a further embodiment the signal sequence comprises SEQ ID NO:24.

In one embodiment the periplasmic signal sequence is encoded by any one of SEQ ID NO: 1, 3, 5, 7, 9, 11, 13, 15, 17, 19, 21 or 23. In a further embodiment the periplasmic signal sequence is encoded by SEQ ID NO:23.

In one embodiment the polynucleotide comprises an inducible promoter.

In one embodiment step b) comprises a step of concentrating the host cell by centrifugation. Optionally this involves centrifuging the cells at between 5000×g and 8000×g, 6000×g and 7000×g or around 6500×g. Optionally the cells are centrifuged for between 30 minutes and 2 hours, optionally the cells are centrifuged for around 1 hour.

In one embodiment step a) takes place at a pH of between 4.5 and 8.5, between 5.0 and 8.0, between 5.5 and 7.5, between 5.0 and 7.0, between 4.5 and 6.5 or between 6.0 and 7.0, or around pH 6.0.

In one embodiment step a) takes place at a temperature of between 20° C. and 40° C. between 25° C. and 35° C., between 27° C. and 32° C. or around 28° C.

In one embodiment the level of dissolved oxygen within the culture for the majority of step a) is between 5% and 40%, between 10% and 30%, between 15% and 25% or around 20%.

In one embodiment step a) is carried out at a Kla of between 10-1000 h$^{-1}$. KLa is a measure of the rate at which oxygen enters the culture. The higher the KLa, the greater the rate at which oxygen is introduced into the culture.

KLa can be measured as follows. The method involves setting up the fermenter with the conditions of medium volume, temperature, pressure, agitation and aeration for which the KLa is to be measured, gassing out by replacing the air with nitrogen gas, gassing in by restoring air aeration and measuring the rate at which pO2 returns to its steady state level.

$$\ln(100-pO2) = -KLa \cdot T + C$$

By plotting ln(100−pO2) against time, the gradient (or angular coefficient) of the line is −KLa. pO2 is the % dissolved oxygen in the broth, T is time, and C is a constant.

The KLa of a fermentation step is influenced by a number of factors including the amount of agitation of the culture and the aeration rate of the culture. A constant KLa may be maintained while for instance decreasing the agitation of the culture and increasing the aeration rate or vice versa. However, in an embodiment, both the agitation of the culture and the aeration rate are constant during the fermentation step.

Step a) and/or step a(i)) take place, for example, at a KLa of between 10-1000 h$^{-1}$, 10-200 h$^{-1}$, 10-150 h$^{-1}$, 10-100 h$^{-1}$, 10-80 h$^{-1}$, 10-50 h$^{-1}$, 10-40 h$^{-1}$, 10-30 h$^{-1}$, 20-150 h$^{-1}$, 20-100 h$^{-1}$, 20-50 h$^{-1}$, 20-60 h$^{-1}$, 20-80 h$^{-1}$, 20-30 h$^{-1}$, 20-40 h$^{-1}$, 30-60 h$^{-1}$, 60-80 h$^{-1}$, 60-150 h$^{-1}$ or 60-200 h$^{-1}$.

In one embodiment the fermentation medium comprises a medium selected from the group consisting of CY, SOC, or a similar medium. In one embodiment the medium is CY or SOC.

In one embodiment step a(i)) comprises addition of an inducing agent. An inducing agent is a compound which is added to the culture, wherein on addition of the inducing agent the rate of protein expression increases. In one embodiment the inducing agent is IPTG.

In one embodiment the process comprises a further step d) of purifying a recombinant protein (such as the bacterial toxoid). In an embodiment step d) involves cell purification using chromatography. In an embodiment the chromatography technique is affinity chromatography, gel filtration, high pressure liquid chromatography (HPLC) or ion exchange chromatography. Optionally the affinity chromatography uses an affinity tag purification column, an antibody purification column, a lectin affinity column, a prostaglandin purification column or a streptavidin column. Optionally the HPLC uses an ion exchange column, a reverse phase column or a size exclusion column. Optionally the ion exchange column is an anion exchange column or a cation exchange column.

In one embodiment the process further comprises a step e) of conjugating a recombinant protein (such as the bacterial toxoid) to a saccharide.

In an embodiment the saccharide is a bacterial saccharide. For example the bacterial saccharide is a capsular saccharide originating from S. pneumoniae, H. influenzae, S. aureus, E. faecalis, E. faecium, Salmonella or S. epidermis. As defined herein a "saccharide" may be either an oligosaccharide or a polysaccharide.

In one embodiment the bacterial saccharide is an S. pneumoniae capsular saccharide selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F. In one embodiment the bacterial saccharide is Haemophilus influenzae b (Hib) polysaccharide or oligosaccharide.

The conjugation may occur by any known coupling technique. The conjugation method may rely on activation of the saccharide with 1-cyano-4-dimethylamino pyridinium tetrafluoroborate (CDAP) to form a cyanate ester. The activated saccharide may thus be coupled directly or via a spacer (linker) group to an amino group on the carrier protein. For example, the spacer could be cystamine or cysteamine to give a thiolated polysaccharide which could be coupled to the carrier via a thioether linkage obtained after reaction with a maleimide-activated carrier protein (for example using GMBS) or a haloacetylated carrier protein (for example using iodoacetimide [e.g. ethyl iodoacetimide HCl] or N-succinimidyl bromoacetate or SIAB, or SIA, or SBAP). Preferably, the cyanate ester (optionally made by CDAP chemistry) is coupled with hexane diamine or ADH and the amino-derivatised saccharide is conjugated to the carrier protein using carbodiimide (e.g. EDAC or EDC) chemistry via a carboxyl group on the protein carrier. Such conjugates are described in PCT published application WO 93/15760 Uniformed Services University and WO 95/08348 and WO 96/29094.

Other suitable techniques use carbodiimides, hydrazides, active esters, norborane, p-nitrobenzoic acid, N-hydroxysuccinimide, S-NHS, EDC, TSTU. Many are described in WO 98/42721. Conjugation may involve a carbonyl linker which may be formed by reaction of a free hydroxyl group of the saccharide with CDI (Bethell at al J. Biol. Chem. 1979, 254; 2572-4, Hearn et al J. Chromatogr. 1981. 218; 509-18) followed by reaction with a protein to form a carbamate linkage. This may involve reduction of the anomeric terminus to a primary hydroxyl group, optional protection/deprotection of the primary hydroxyl group' reaction of the primary hydroxyl group with CDI to form a CDI carbamate intermediate and coupling the CDI carbamate intermediate with an amino group on a protein. The conjugates can also be prepared by direct reductive amination methods as described in U.S. Pat. No. 4,365,170 Jennings) and U.S. Pat. No. 4,673,574 (Anderson). Other methods are described in EP-0-161-188, EP-208375 and EP-0-477508. A further method involves the coupling of a cyanogen bromide (or CDAP) activated saccharide derivatised with adipic acid dihydrazide (ADH) to the protein carrier by Carbodiimide condensation (Chu C. et al Infect. Immunity, 1983 245 256), for example using EDAC.

In an embodiment, a hydroxyl group (preferably an activated hydroxyl group for example a hydroxyl group activated to make a cyanate ester [e.g. with CDAP]) on a saccharide is linked to an amino or carboxylic group on a protein either directly or indirectly (through a linker). Where a linker is present, a hydroxyl group on a saccharide is preferably linked to an amino group on a linker, for example by using CDAP conjugation. A further amino group in the linker for example ADH) may be conjugated to a carboxylic acid group on a protein, for example by using carbodiimide chemistry, for example by using EDAC. In an embodiment, the pneumococcal capsular saccharide(s) is conjugated to the linker first before the linker is conjugated to the carrier protein. Alternatively the linker may be conjugated to the carrier before conjugation to the saccharide.

In general the following types of chemical groups on a protein carrier can be used for coupling/conjugation:

A) Carboxyl (for instance via aspartic acid or glutamic acid). In one embodiment this group is linked to amino groups on saccharides directly or to an amino group on a linker with carbodiimide chemistry e.g. with EDAC.

B) Amino group (for instance via lysine). In one embodiment this group is linked to carboxyl groups on saccharides directly or to a carboxyl group on a linker with carbodiimide chemistry e.g. with EDAC. In another embodiment this group is linked to hydroxyl groups activated with CDAP or CNBr on saccharides directly or to such groups on a linker; to saccharides or linkers having an aldehyde group; to saccharides or linkers having a succinimide ester group.

C) Sulphydryl (for instance via cysteine). In one embodiment this group is linked to a bromo or chloro acetylated saccharide or linker with maleimide chemistry. In one embodiment this group is activated/modified with bis diazobenzidine.

D) Hydroxyl group (for instance via tyrosine). In one embodiment this group is activated/modified with bis diazobenzidine.

E) Imidazolyl group (for instance via histidine). In one embodiment this group is activated/modified with bis diazobenzidine.

F) Guanidyl group (for instance via arginine).

G) Indolyl group (for instance via tryptophan).

On a saccharide, in general the following groups can be used for a coupling: OH, COOH or NH2. Aldehyde groups can be generated after different treatments known in the art such as: periodate, acid hydrolysis, hydrogen peroxide, etc.

Direct Coupling Approaches:

Saccharide-OH+CNBr or CDAP→cyanate ester+ NH2-Prot→conjugate

Saccharide-aldehyde+NH2-Prot→Schiff base+ NaCNBH3→conjugate

Saccharide-COOH+NH2-Prot+EDAC→conjugate

Saccharide-NH2+COOH-Prot+EDAC→conjugate

Indirect Coupling Via Spacer (Linker) Approaches:

Saccharide-OH+CNBr or CDAP→cyanate ester+ NH2-NH2→saccharide-NH2+COOH-Prot+ EDAC→conjugate Saccharide-OH+CNBr or CDAP→cyanate ester+ NH2-SH→saccharide-SH+SH-Prot (native Protein with an exposed cysteine or obtained after modification of amino groups of the protein by SPDP for instance)→saccharide-S—S-Prot Saccharide-OH+CNBr or CDAP→cyanate ester+ NH2-SH→saccharide-SH+maleimide-Prot (modification of amino groups)→conjugate Saccharide-OH+CNBr or CDAP→cyanate ester+ NH2-SH→Saccharide-SH+haloacetylated-Prot→Conjugate Saccharide-COOH+EDAC+NH2-NH2→saccharide-NH2+EDAC+COOH-Prot→conjugate Saccharide-COOH+EDAC+NH2-SH→saccharide-SH+SH-Prot (native Protein with an exposed cysteine or obtained after modification of amino groups of the protein by SPDP for instance)→saccharide-S—S-Prot Saccharide-COOH+EDAC+NH2-SH→saccharide-SH+maleimide-Prot (modification of amino groups)→conjugate Saccharide-COOH+EDAC+NH2-SH→Saccharide-SH+haloacetylated-Prot-→Conjugate Saccharide-Aldehyde+NH2-NH2→saccharide-NH2+ EDAC+COOH-Prot→conjugate Note: instead of EDAC above, any suitable carbodiimide may be used.

In summary, the types of protein carrier chemical group that may be generally used for coupling with a saccharide are amino groups (for instance on lysine residues), COOH groups (for instance on aspartic and glutamic acid residues) and SH groups (if accessible) (for instance on cysteine residues.

In one embodiment the pH of step a) is lower than the pH of step a(i)). In one embodiment the temperature of step a) is higher than the temperature of step a(i)). In one embodiment the substrate feed rate of step a) is higher than the substrate feed of rate a(i)).

In a further embodiment the pH of step a) ranges from 5.0-7.0, 5.0-6.0, 6.0-7.0 or from 6.5-7.0.

In an embodiment the pH in step a(i)) is maintained. In an embodiment the pH is maintained at greater than pH 6.5, 7.0, 7.5, 8.0, 8.5, 9.0, 9.5, 10.0 or between 6.5 and 10.0, 6.5 and 9.5, 6.5 and 9.0, 6.5 and 8.5, 6.5 and 7.5, 6.5 and 7.0, 7.0 and 10.0, 7.0 and 9.5, 7.0 and 9.0, 7.0 and 8.5, 7.0 and 8.0, 7.0 and 7.5, 7.5 and 10.0, 7.5 and 9.5, 7.5 and 9.0, 7.5 and 8.5, 7.5 and 8.0, 8.0 and 10.0, 8.0 and 9.5, 8.0 and 9.0, 8.0 and 8.5, 8.5 and 10.0, 8.5 and 9.5, 8.5 and 9.0, 8.0 and 8.5, 8.5 and 10.0, 8.5 and 9.5, 8.5 and 9.0, 9.0 and 10.0, 9.0 and 9.5 or 9.5 and 10.0. In a further embodiment the pH is maintained using a buffer from the group consisting of phosphate buffer, Tris buffer and histidine buffer. Optionally the buffer is at a concentration of 10-200 mM, 50-100 mM, 100-200 mM, 10-50 mM or 50-150 mM. Optionally the buffer is phosphate buffer at 80-120 mM, 80-100 mM or 100 mM.

In one embodiment the pH in step a(i)) is at least, exactly or approximately 2.0, 1.5, 1.0, 0.5, 0.3, 0.2 or 0.1 pH units higher than the pH in step a).

Optionally this decrease in pH is achieved by addition of base for instance sodium hydroxide or ammonia.

In an embodiment the temperature of step a) is higher than the temperature of step a(i)). In an embodiment step a) of the process is carried out at a temperature of 20-40° C. Optionally step a(i)) of the process is carried out at a temperature of 20-28° C., 21-27° C., 22-26° C., 23-24° C., 21-24° C., or 22-23° C.

In a further embodiment the substrate feed rate in step a(i)) is maintained between 5% and 90%, 20% and 80% or 20% and 30% of the substrate feed rate maintained during step a).

In one embodiment the process is carried out in a fermentor. In one embodiment antifoam agent is added in step a) and/or step a(i). In a further embodiment a foam probe or mechanical foam breaker is used in step a) and/or step a(i)). In a further embodiment antifoam agent, and a foam probe or mechanical foam breaker are used in step a) and/or step a(i)).

In one embodiment the fermentor contains 10-5000 liters of culture. In a further embodiment the fermentor contains at least 500 liters of culture, in a further embodiment the fermentor contains at least 1000 liters of culture. In a further embodiment the fermentor contains between 50-1000, 100-500, or 100-200 liters of culture. In a further embodiment the fermentor contains around 150 liters of culture.

In a further embodiment the process further comprises a step f) of mixing a recombinant protein (such as the bacterial toxoid) with further antigens. In one embodiment the further antigens are cancer, viral or bacterial antigens. In one embodiment the vaccine or immunogenic composition may comprise antigens derived from S. pneumoniae, H. influenzae, N. meningitides, E. coli, C. trachomatis, M. cattarhalis, tetanus, diphtheria, pertussis, S. epidermidis, Enterococci, or S. aureus.

In one embodiment a recombinant protein of the invention (such as the bacterial toxoid of the invention) is mixed with a pharmaceutically acceptable excipient. In a further embodiment a recombinant protein (such as the bacterial toxoid of the invention) is mixed with an adjuvant. The choice of a suitable adjuvant to be mixed with bacterial toxins or conjugates made using the processes of the invention is within the knowledge of the person skilled in the art. Suitable adjuvants include an aluminium salt such as aluminium hydroxide, aluminium hydroxide gel or aluminum phosphate or alum, but may also be other metal salts such as those of calcium, magnesium, iron or zinc, or may be an insoluble suspension of acylated tyrosine, or acylated sugars, cationically or anionically derivatized saccharides, or polyphosphazenes.

In a further aspect of the invention there is provided a recombinant protein (such as a bacterial toxoid of the invention) obtainable by the process of the invention. In a further aspect of the invention there is provided a recombinant protein (such as a bacterial toxoid of the invention) obtained by the process of the invention.

In a further aspect of the invention there is provided an immunogenic composition comprising a recombinant protein of the invention (such as the bacterial toxoid of the invention) and a pharmaceutically acceptable excipient. In one embodiment the immunogenic composition of the invention comprises further antigens. Optionally these further antigens are antigens derived from S. pneumoniae, H. influenzae, N. meningitides, E. coli, C. trachomatis, M. cattarhalis, tetanus, diphtheria, pertussis, S. epidermidis, Enterococci, or S. aureus.

In one embodiment there is provided an immunogenic composition of the invention for use in the prevention or treatment of disease. In a further embodiment there is provided the immunogenic composition of the invention for use in the prevention or treatment of bacterial, viral or cancer disease.

In a further aspect of the invention there is provided a vaccine comprising the immunogenic composition of the invention.

The vaccine preparations containing immunogenic compositions of the present invention may be used to protect or treat a mammal susceptible to infection, by means of administering said vaccine via systemic or mucosal route. These administrations may include injection via the intramuscular, intraperitoneal, intradermal or subcutaneous routes; or via mucosal administration to the oral/alimentary, respiratory, genitourinary tracts. Intranasal administration of vaccines for the treatment of pneumonia or otitis media is preferred (as nasopharyngeal carriage of pneumococci can be more effectively prevented, thus attenuating infection at its earliest stage). Although the vaccine of the invention may be administered as a single dose, components thereof may also be co-administered together at the same time or at different times (for instance pneumococcal saccharide conjugates could be administered separately, at the same time or 1-2 weeks after the administration of the bacterial protein component of the vaccine for optimal coordination of the immune responses with respect to each other). In addition to a single route of administration, 2 different routes of administration may be used. For example, saccharides or saccharide conjugates may be administered IM (or ID) and bacterial proteins may be administered IN (or ID). In addition, the vaccines of the invention may be administered IM for priming doses and IN for booster doses.

The content of toxins in the vaccine will typically be in the range 1-100 µg, preferably 5-50 µg, most typically in the range 5-25 µg. Following an initial vaccination, subjects may receive one or several booster immunizations adequately spaced. Vaccine preparation is generally described in Vaccine Design ("The subunit and adjuvant approach" (eds Powell M. F. & Newman M. J.) (1995) Plenum Press New York). Encapsulation within liposomes is described by Fullerton, U.S. Pat. No. 4,235,877.

In a further aspect there is provided a use of the immunogenic composition or vaccine of the invention in the prevention or treatment of disease. In a one embodiment there is provided a use of the immunogenic composition or vaccine of the invention in the prevention of a disease selected from the group consisting of cancer, viral and bacterial disease.

In a further aspect there is provided a use of the immunogenic composition or the vaccine of the invention in the manufacture of a medicament for the prevention or treatment of disease. In a further embodiment there is provided a use of the immunogenic composition or the vaccine of the invention in the manufacture of a medicament for the prevention or treatment of a disease selected from the group consisting of cancer, viral and bacterial disease.

In a further aspect there is provided a method of preventing or treating disease comprising administering the immunogenic composition or vaccine of the invention to a patient. In a further embodiment there is provided a method of preventing or treating a disease selected from the group consisting of cancer, viral and bacterial disease comprising administering the immunogenic composition or vaccine of the invention to a patient.

The terms "comprising", "comprise" and "comprises" herein is intended by the inventors to be optionally substitutable with the terms "consisting of", "consist of", and "consists of", respectively, in every instance.

Unless otherwise explained, all technical and scientific terms used herein have the same meaning as commonly understood by one of ordinary skill in the art to which this disclosure belongs. Definitions of common terms in molecular biology can be found in Benjamin Lewin, *Genes V*, published by Oxford University Press, 1994 (ISBN 0-19-854287-9); Kendrew at al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

The singular terms "a," "an," and "the" include plural references unless context clearly indicates otherwise. Similarly, the word "or" is intended to include "and" unless the context clearly indicates otherwise. The term "plurality" refers to two or more. It is further to be understood that all base sizes or amino acid sizes, and all molecular weight or molecular mass values, given for nucleic acids or polypeptides are approximate, and are provided for description. Additionally, numerical limitations given with respect to concentrations or levels of a substance, such as an antigen, are intended to be approximate. Thus, where a concentrations is indicated to be at least (for example) 200 pg, it is intended that the concentration be understood to be at least approximately (or "about" or "~") 200 pg.

Embodiments of the invention are further described in the following numbered clauses.

1. A process for producing a recombinant protein comprising the steps of:
   a) growing a culture of a host cell in a fermentation medium, wherein the host cell is transformed with a polynucleotide, and wherein the polynucleotide encodes the recombinant protein and a periplasmic signal sequence;
   b) maturing the host cell; and
   c) extracting the recombinant protein from the host cell.
2. A process for producing a recombinant protein comprising the steps of:
   a) providing a host cell wherein the host cell is transformed with a polynucleotide, and wherein the polynucleotide encodes the recombinant protein and a periplasmic signal sequence and wherein the host cell comprises the recombinant protein expressed in the periplasm;
   b) maturing the host cell; and
   c) extracting the recombinant protein from the host cell.
3. The process of clause 1 or 2 further comprising a step a(i)) of inducing expression of the recombinant protein.
4. The process of any one of clauses 1-3 wherein step b) comprises subjecting the host cell to a pH shock.
5. The process of clause 4 wherein the pH shock comprises changing the pH of the fermentation medium by more than 0.2 pH units or more than 0.5 pH units.
6. The process of clause 5 wherein the pH shock comprises increasing the pH of the fermentation medium by more than 0.2 pH units or more than 0.5 pH units.
7. The process of clause 5 wherein the pH shock comprises decreasing the pH of the fermentation medium by more than 0.2 pH units or more than 0.5 pH units.
8. The process of any preceding clause wherein the pH shock comprises changing the pH of the fermentation medium by between 0.1 and 2.0 pH units or between 0.2 and 1.0 pH units.
9. The process of any one of clauses 5, 6 or 8 wherein the pH shock comprises increasing the pH of the fermentation medium by between 0.1 and 2.0 pH units or between 0.2 and 1.0 pH units.
10. The process of any one of clauses 5, 7 or 8 wherein the pH shock comprises decreasing the pH of the fermentation medium by between 0.1 and 2.0 pH units or between 0.2 and 1.0 pH units.
11. The process of any one of clauses 5, 6, 8 or 9 wherein the pH shock is achieved by addition of a base.
12. The process of clause 11 wherein the base is ammonium hydroxide ($NH_4OH$) or sodium hydroxide (NaOH).
13. The process of any one of clauses 5, 7, 8, or 10 wherein the pH shock is achieved by addition of an acid.
14. The process of clause 13 wherein the acid is phosphoric acid ($H_3PO_4$).
15. The process of any preceding clause wherein step b) comprises an incubation step and wherein the incubation step comprises incubating the host cell for at least 5 minutes, at least 10 minutes, at least 30 minutes, at least 1 hour or at least 2 hours at a temperature above 0° C., above 10° C. above 20° C. or above 23° C.
16. The process of clause 15 wherein the incubation step comprises incubating the host cell for between 10 minutes and 1 year, between 10 minutes and 6 months, between 10 minutes and 12 hours, between 10 minutes and 6 hours or between 10 minutes and 2 hours.
17. The process of clause 15 or 16 wherein the incubation step comprises incubating the host cell at a temperature between 20° C.-40° C.
18. The process of any one of clauses 15-17 wherein the incubation step occurs at a temperature around 23° C.
19. The process of any one of clauses 15-18 wherein step a) has a first feed rate and step b) has a second feed rate and wherein the second feed rate is lower than the first feed rate.
20. The process of any one of clauses 15-19 wherein there is no feed addition during the incubation step.
21. The process of any one of clauses 15-20 wherein there is no pH control during the incubation step.
22. The process of any preceding clause wherein step b) comprises subjecting the host cell to a temperature below 0° C. for at least 1 hour, 2 hours, 5 hours, 12 hours, 24 hours, 1 day, 2 days or 5 days.
23. The process of any preceding clause wherein step b) comprises freezing the host cell for at least 1 hour, 2 hours, 5 hours, 12 hours, 24 hours, 1 day, 2 days or 5 days.
24. The process of clause 22 or 23 wherein step b) comprises freezing the host cell at a temperature below −10° C., −20° C. or −70° C.
25. The process of any one of clauses 22-24 wherein step b) further comprises thawing the cells.
26. The process of any preceding clause wherein step b) comprises subjecting the host cell to a pH shock followed by an incubation step wherein the incubation step comprises incubating the host cell for at least 5 minutes, at least 10 minutes, at least 30 minutes, at least 1 hour or at least 2 hours at a temperature above 0° C., above 10° C. above 20° C. or above 23° C.
27. The process of any one of clauses 1-26 wherein step b) comprises an incubation step wherein the incubation step comprises incubating the host cell for at least 5 minutes, at least 10 minutes, at least 30 minutes, at least 1 hour or at least 2 hours at a temperature above 0° C., above 10° C. above 20° C. or above 23° C., followed by subjecting the host cell to a pH shock.
28. The process of any preceding clause wherein step b) comprises an incubation step wherein the incubation step comprises incubating the host cell for at least 5 minutes, at least 10 minutes, at least 30 minutes, at least 1 hour or at least 2 hours at a temperature above 0° C., above 10° C. above 20*C or above 23° C. followed by freezing the host cell for at least 1 hour, 2 hours, 5 hours, 12 hours, 24 hours, 1 day, 2 days or 4 days.
29. The process of any preceding clause wherein step b) comprises subjecting the host cell to pH shock followed by freezing the host cell for at least 1 hour, 2 hours, 5 hours, 12 hours, 24 hours, 1 day, 2 days or 4 days.
30. The process of any one of clauses 1-26 or 28-29 wherein step b) comprises subjecting the host cell to a pH shock followed by an incubation step wherein the incubation step comprises incubating the host cell for at least 5 minutes, at least 10 minutes, at least 30 minutes, at least 1 hour or at least 2 hours at a temperature above 0° C., above 10° C. or above 20° C. followed by freezing the host cell for at least 1 hour, 2 hours, 5 hours, 12 hours, 24 hours, 1 day, 2 days or 4 days.
31. The process of any one of clauses 1-25 or 27-29 wherein step b) comprises an incubation step wherein the incubation step comprises incubating the host cell for at least 5 minutes, at least 10 minutes, at least 30 minutes, at least 1 hour or at least 2 hours at a temperature above 0° C., above 10° C. or above 20° C., followed by subjecting the host cell to a pH shock followed by freezing the host cell for at least 1 hour, 2 hours, 5 hours, 12 hours, 24 hours, 1 day, 2 days or 4 days.

32. The process of any preceding clause wherein the host cell is a gram negative host cell.

33. The process of clause 32 wherein the gram negative host cell is selected from the group consisting of *E. coli, Acinetobacter, Actinobacillus, Bordetella, Brucella, Campylobacter, Cyanobacteria, Enterobacter, Erwinia, Franciscella, Helicobacter, Hemophilus, Klebsiella, Legionella, Moraxella, Neisseria, Pasteurella, Pseudomonas, Proteus, Salmonella, Serratia, Shigella, Treponema, Vibrio*, and *Yersinia*.

34. The process of clause 32 or 33 wherein the gram negative host cell is selected from the group consisting of *E. coli, Pseudomonas*, and *Moraxella*.

35. The process of any one of clauses 32-34 wherein the gram negative host cell is *E. coli*.

36. The process of any preceding clause wherein step c) comprises osmotic shock.

37. The process of any preceding clause wherein the host cell is alive during step b).

38. The process of any preceding clause wherein the recombinant protein comprises a bacterial, viral or cancer antigen.

39. The process of any preceding clause wherein the recombinant protein is a prokaryotic protein.

40. The process of any preceding clause wherein the recombinant protein is a soluble protein.

41. The process of any preceding clause wherein the recombinant protein is a surface associated protein.

42. The process of any one of clauses 1-49 wherein the recombinant protein is a toxoid.

43. The process of any preceding clause wherein the recombinant protein is derived from *C. diphtheriae, S. pneumoniae, H. influenzae, Moraxella, N. meningitidis, S. aureus, E. faecalis, E. faecium, Salmonella, C. trachomatis*, or *S. epidermidis*.

44. The process of any preceding clause 42 or 43 wherein the recombinant protein is diphtheria toxoid.

45. The process of clause 42 or 43 wherein the recombinant protein is CRM197.

46. The process of any preceding clause wherein the periplasmic signal sequence is a heterologous signal sequence.

47. The process of any preceding clause wherein the periplasmic signal sequence is:
   a) any one of SEQ ID NO: 2, 4, 6, 8, 10, 12, 14, 18, 20, 22, 24, or 26;
   b) variants of SEQ ID NO: 2, 4, 6, 8, 10, 12, 14, 18, 20, 22, 24, or 26 containing 1, 2, or 3 point mutations, insertions or deletions; or
   c) fragments of at least 10 amino acids of SEQ ID NO: 2, 4, 6, 8, 10, 12, 14, 18, 20, 22, 24, or 26.

48. The process of clause 47 wherein the periplasmic signal sequence is:
   a) any one of SEQ ID NO: 2, 4, 10, 12, 14, 16, 18, 20, 22, 24, or 26;
   b) variants of SEQ ID NO: 2, 4, 10, 12, 14, 16, 18, 20, 22, 24, or 26 containing 1, 2, or 3 point mutations, insertions or deletions; or
   c) fragments of at least 10 amino acids of SEQ ID NO: 2, 4, 10, 12, 14, 16, 18, 20, 22, 24, or 26.

49. The process of clause 47 wherein the periplasmic signal sequence is:
   a) any one of SEQ ID NO: 2, 4, 10, 12, 14, 16, 18, 20, 22, or 24;
   b) variants of SEQ ID NO: 2, 4, 10, 12, 14, 16, 18, 20, 22, or 24 containing 1, 2, or 3 point mutations, insertions or deletions; or
   c) fragments of at least 10 amino acids of SEQ ID NO: 2, 4, 10, 12, 14, 16, 18, 20, 22, or 24.

50. The process of any preceding clause wherein the periplasmic signal sequence is encoded by any one of SEQ ID NO: 1, 3, 5, 7, 9, 11, 13, 15, 17, 19, 21 or 23.

51. The process of clause 50 wherein the periplasmic signal sequence is encoded by any one of SEQ ID NO: 1, 3, 9, 11, 13, 15, 17, 19, 21, 23 or 25.

52. The process of clause 50 wherein the periplasmic signal sequence is encoded by any one of SEQ ID NO: 1, 3, 9, 11, 13, 15, 17, 19, 21 or 23.

53. The process of any preceding clause wherein the polynucleotide comprises an inducible promoter.

54. The process of any preceding clause wherein step b) comprises a step of concentrating the host cell by centrifugation.

55. The process of any preceding clause wherein step a) takes place at a pH of between 5.0 and 8.0 or between 6.0 and 7.0.

56. The process of any preceding clause wherein step a) takes place at a temperature of between 20° C. and 40° C.

57. The process of any preceding clause wherein the level of dissolved oxygen within the culture for the majority of step a) is between 10% and 30%.

58. The process of any preceding clause wherein step a) is carried out at a Kla of between 10-1000 $h^{-1}$.

59. The process of any preceding clause wherein the fermentation medium comprises a medium selected from the group consisting of CY, SOC or a similar medium.

60. The process of clause 3 wherein step a(i)) comprises addition of an inducing agent and/or modifying the temperature of the fermentation medium.

61. The process of clause 60 wherein the inducing agent is IPTG.

62. The process of clause 61 wherein step a(i)) comprises modifying the temperature of the fermentation medium by more than 2° C., more than 5° C., more than 10° C. or more than 15° C.

63. The process of any preceding clause further comprising a step d) of purifying the recombinant protein.

64. The process of any preceding clause further comprising a step e) of conjugating the recombinant protein to a saccharide.

65. The process of clause 64 wherein the saccharide is a bacterial saccharide originating from *S. pneumoniae, H. influenzae, N. meningitidis, S. aureus, E. faecalis, E. faecium, Salmonella*, or *S. epidermidis*.

66. The process of clause 65 wherein the bacterial saccharide is an *S. pneumoniae* capsular saccharide selected from the group consisting of 1, 2, 3, 4, 5, 6A, 6B, 7F, 8, 9N, 9V, 10A, 11A, 12F, 14, 15B, 17F, 18C, 19A, 19F, 20, 22F, 23F and 33F.

67. The process of clause 66 wherein the bacterial saccharide is *Haemophilus influenzae* b (Hib) polysaccharide or oligosaccharide.

68. The process of clause 2 wherein the pH of step a) is lower than the pH of step a(i)).

69. The process of clause 2 wherein the temperature of step a) is higher than the temperature of step a(i)).

70. The process of clause 2 wherein the substrate feed rate of step a) is higher than the substrate feed rate of step a(i)).

71. The process of any preceding clause wherein the process is carried out in a fermentor.

72. The process of any preceding clause wherein an antifoam agent is added in step a) and/or step a(i)).
73. The process of any preceding clause wherein a foam probe or a mechanical foam breaker is used in step a) and/or step a(i)).
74. The process of clause 71 wherein the fermentor contains 10-5000 liters of culture.
75. The process of any one of clauses 74 wherein the fermentor contains between 100-200 liters or around 150 liters of culture.
76. The process of any preceding clause further comprising a step f) of mixing the recombinant protein with further antigens.
77. The process of any preceding clause wherein the recombinant protein is mixed with a pharmaceutically acceptable excipient.
78. The process of any preceding clause wherein the recombinant protein is mixed with an adjuvant.
79. A recombinant protein obtainable by the process of any preceding clause.
80. A recombinant protein obtained by the process of any one of clauses 1-78.
81. An immunogenic composition comprising the recombinant protein of clause 79 or 80 and a pharmaceutically acceptable excipient.
82. The immunogenic composition of clause 81 comprising further antigens.
83. The immunogenic composition of clause 81 or 82 for use in the prevention or treatment of disease.
84. A vaccine comprising the immunogenic composition of clause 81-83.
85. A use of the immunogenic composition of clause 81-83 or the vaccine of clause 84 in the prevention or treatment of disease.
86. A use of the immunogenic composition of clause 81-83 or the vaccine of clause 84 in the manufacture of a medicament for the prevention or treatment of disease.
87. A method of preventing or treating disease comprising administering the immunogenic composition of clause 81-83 or the vaccine of clause 84 to a patient.

EXAMPLES

Example 1

*Escherichia coli* B2355 Pre-Culture

A pre-culture was prepared using a frozen seed culture of *Escherichia coli* strain B2355. This strain is a B834(DE3) strain transformed with a pET26b derivative containing a sequence coding for a fusion protein between the signal peptide of FlgI from *E. coli* (SEQ ID NO:23) and CRM197 (SEQ ID NO:27). The seed culturability was determined as approximately $1 \times 10^{10}$ colony forming units per ml.

The seed culture was thawed to room temperature and 400 µl were used to inoculate a 2 liter Erlenmeyer flask containing 400 ml of preculture medium (adapted from Zabriskie et al. (J. Ind. Microbiol. 2:87-95 (1987))).

The inoculated flask was then incubated at 37° C. (±1° C.) and 200 rpm. The pre-culture phase was stopped when the culture gained an optical density at 650 nm ($OD_{650nm}$) of between 0.5 and 1.5, (around 5 h of incubation). The pre-culture was used to inoculate medium in a fermenter as soon as the culture was stopped (example 2).

Example 2

20 L Scale Fedbatch Fermentation

A 20 liter fermenter (Biolafitte) was used. Nine liters of batch phase medium were aseptically transferred into the fermenter (adapted from Zabriskie et al. (J. Ind. Microbiol. 2:87-95 (1987))). The pH of the medium was adjusted to 6.8 with base addition. Three ml of undiluted irradiated antifoam (SAG471) was also added to the fermenter. The temperature (28° C.), head pressure (0.5 bar), aeration rate (20 liters sparged air per minute) and initial agitation speed (300 rpm) were then set prior to inoculation. The level of dissolved oxygen in these conditions was 100%. The head pressure and aeration rate were maintained at a constant level during the fermentation.

Inoculation was achieved by the addition of about 20 ml of pre-culture (prepared as described in Example 1).

During batch phase (0-15 h), the temperature was maintained at 28° C. The level of dissolved oxygen was set at 20%. The level of dissolved oxygen (DO) was regulated by increasing stirring when the DO fell below 20%. Glucose exhaustion resulted in an increase in DO and a concomitant decrease in stirring.

After 15 h fermentation, additional substrate was added according to the following feed addition profile:

TABLE 1

| Fermentation time (h) | Additional substrate feed rate (ml/min) | Cumulative weight fed (g) |
| --- | --- | --- |
| 0 | 0.000 | 0 |
| 1 | 0.000 | 0 |
| 2 | 0.000 | 0 |
| 3 | 0.000 | 0 |
| 4 | 0.000 | 0 |
| 5 | 0.000 | 0 |
| 6 | 0.000 | 0 |
| 7 | 0.000 | 0 |
| 8 | 0.000 | 0 |
| 9 | 0.000 | 0 |
| 10 | 0.000 | 0 |
| 11 | 0.000 | 0 |
| 12 | 0.000 | 0 |
| 13 | 0.000 | 0 |
| 14 | 0.000 | 0 |
| 15 | 0.000 | 0 |
| 16 | 0.600 | 21 |
| 17 | 1.150 | 81 |
| 18 | 1.150 | 161 |
| 19 | 1.150 | 241 |
| 20 | 1.150 | 321 |
| 21 | 1.150 | 400 |
| 22 | 1.150 | 480 |
| 23 | 1.150 | 560 |
| 24 | 1.150 | 639 |
| 25 | 1.150 | 719 |
| 26 | 1.150 | 799 |
| 27 | 1.150 | 878 |
| 28 | 1.150 | 958 |
| 29 | 1.150 | 1038 |
| 30 | 1.150 | 1117 |
| 31 | 1.150 | 1197 |
| 32 | 1.150 | 1277 |
| 33 | 1.150 | 1357 |
| 34 | 1.150 | 1436 |
| 35 | 1.150 | 1516 |
| 36 | 1.150 | 1596 |
| 37 | 1.150 | 1675 |
| 38 | 1.150 | 1755 |
| 39 | 1.150 | 1835 |
| 40 | 1.150 | 1914 |
| 41 | 1.150 | 1994 |
| 42 | 1.150 | 2074 |

TABLE 1-continued

| Fermentation time (h) | Additional substrate feed rate (ml/min) | Cumulative weight fed (g) |
|---|---|---|
| 43 | 1.150 | 2153 |
| 44 | 1.150 | 2233 |
| 45 | 1.150 | 2313 |
| 46 | 1.150 | 2393 |
| 47 | 0.325 | 2444 |
| 48 | 0.325 | 2466 |
| 49 | 0.325 | 2489 |
| 50 | 0.325 | 2511 |
| 51 | 0.325 | 2534 |
| 52 | 0.325 | 2556 |
| 53 | 0.325 | 2579 |
| 54 | 0.325 | 2601 |
| 55 | 0.325 | 2624 |
| 56 | 0.325 | 2646 |
| 57 | 0.325 | 2669 |
| 58 | 0.325 | 2691 |
| 59 | 0.325 | 2714 |
| 60 | 0.325 | 2736 |
| 61 | 0.325 | 2759 |
| 62 | 0.325 | 2782 |
| 63 | 0.325 | 2804 |
| 64 | 0.325 | 2827 |
| 65 | 0.325 | 2849 |
| 66 | 0.325 | 2872 |
| 67 | 0.325 | 2894 |
| 68 | 0.325 | 2917 |
| 69 | 0.325 | 2939 |
| 70 | 0.325 | 2962 |
| 71 | 0.325 | 2984 |
| 72 | 0.325 | 3007 |

During the fed-batch phase (15-46 h), the pH was maintained at 6.8 by addition of base, the temperature was regulated at 28° C., and the DO level was maintained at 20% through control of the stirring rate.

At 46 hours IPTG was added to a final concentration of 1 mM to induce the bacteria. In addition the pH was increased after 46 hours by addition of base, and the temperature was decreased to 23° C. (these changes may lead to high levels of periplasmic expression). The pH and temperature were maintained during the whole induction phase (46-72 h). The DO level was maintained at 20% by controlling the stirring rate.

At the end of the induction phase (72 h), cell paste was collected by centrifugation (6,500×g, 4° C. for 1 h), and stored at −20° C.

Periplasmic extraction was performed by osmotic shock using a procedure adapted from Chen et al. (Biochem. Eng. J. 19:211-215 (2004) differences described in table 2 below). CRM197 content in the periplasmic and cytoplasmic fractions were assayed by Elisa.

TABLE 2

| | Chen | Method used in example 2 |
|---|---|---|
| Harvest centrifugation | 10 min. 4° C. 8,000xg | 1 h 4° C. 6,500xg |
| Cell pellet washes | twice with RO water | none |
| 1st buffer | TrisHCl 33 mM pH 8.0 + EDTA 0.5 mM + sucrose 20% | TrisHCl 30 mM pH 8.0 + EDTA 0.5 mM + sucrose 20% |
| 2nd buffer | RO water | MgSO4 5 mM |
| Vol 1st buffer | 1.6 | 1 |
| Vol 2nd buffer | 1.6 | 1 |
| Incubation 1st buffer | 10 min. 4° C. agitation | 30 min. RT no shaking |
| Incubation 2nd buffer | 10 min. 4° C. agitation | 30 min. RT no shaking |
| Centrifugation 1st buffer | 10 min. 4° C. 8,000xg | 30 min. RT 15,900xg |
| Centrifugation 2nd buffer | 10 min. 4° C. 8,000xg | 30 min. RT 15,900xg |

FIG. 1 shows a typical fermentation profile with the process parameters monitored during 20 L-scale fed-batch fermentation.

At the end of fermentation, periplasmic CRM197 productivity was assayed by Elisa:

TABLE 3

| Periplasmic | Cytoplasmic | Secretion efficiency |
|---|---|---|
| 3180 mg/L | 394 mg/L | 87% |

This technique demonstrated increased levels of expression and efficiency of secretion.

Example 3

Determination of the Optimum Feed Rates and pH to be Used During the Induction Phase In this experiment response-surface methodology (Rairakhwada et al., J. Ind. Microbiol. 37:195-204 (2010)) was used to determine optimal values for three parameters, in order to maximize periplasmic production of a recombinant protein. The three fermentation parameters investigated were the pH during the growth phase, the pH during induction and the feed rate during induction. Values for these three parameters were chosen according to a Doehlert uniform shell design (Doehlert (Applied Statistics 19:231-239 (1970))). Fifteen fermentations were carried out using the values described in table 5.

The fermentations were carried out using strain B2284, this is a strain of BLR (DE3) cells transformed with a pET26b derivative containing a sequence coding for a fusion protein between the signal peptide of FlgI (SEQ ID NO:23) from *E. coli* and the mature part of CRM197 (SEQ ID NO:27).

For each fermentation, the seed culture was thawed to room temperature and 500 µl was used to inoculate a 2 liter Erlenmeyer flask containing 400 ml of preculture medium (adapted from Zabriskie et al. (J. Ind. Microbiol. 2:87-95 (1987))).

The inoculated flask was then incubated at 37° C. (±1° C.) and 200 rpm. The pre-culture was stopped when the optical density at 650 nm ($OD_{650nm}$) reached around 2.5, (around 6 h of incubation). The pre-culture was used to inoculate medium in a fermenter as soon as the culture was stopped (adapted from Zabriskie et al. (J. Ind. Microbiol. 2:87-95 (1987)).

A 20 liter fermenter (Biolafitte) was used. Nine liters of batch phase medium were aseptically transferred into the fermenter. The pH of the medium was adjusted to the target value (Table 5) with base addition. 3 ml of undiluted irradiated antifoam (SAG 471) was also added to the fermenter. The temperature (28° C.), head pressure (0.5 bar), aeration rate (20 liters sparged air per minute) and initial agitation speed (300 rpm) were then set prior to inoculation. The level of dissolved oxygen (DO) in these conditions was 100%. The head pressure and aeration rate were maintained at a constant level during the fermentation.

During batch phase (0-15 h), the temperature was maintained at 28° C. The level of dissolved oxygen was set at 20% and regulated by increasing stirring when the DO fell below 20%.

During the fed-batch phase (15-46 h), the pH was maintained according to one of the conditions described in table 5 by addition of base. The temperature was regulated at 28° C. The stirring rate was maintained at a constant setpoint (maximum 800 rpm), and the DO level was maintained at 20% by automatic addition of concentrated feed solution (adapted from Zabriskie et al. (J. Ind. Microbiol. 2:87-95 (1987)) when the DO increased above 20%.

When the culture reached an $OD_{650nm}$ around 90, the pH setpoint was modified according to one of the conditions described in table 5 by base or acid addition and the temperature was decreased to 23° C. Once these conditions were achieved IPTG was added to a final concentration of 1 mM. The pH and temperature were maintained during the whole induction phase (24 h). A constant substrate feed rate was used during the whole induction phase, according to one of the conditions described in table 4. The DO level was maintained at 20% by controlling the stirring rate.

At the end of the induction phase, cell paste was collected by centrifugation (typically 6,500×g, 4° C. for 1 h), and stored at −20° C.

Periplasmic extraction was performed by osmotic shock using a procedure adapted from Chen et al. (Biochem. Eng. J. 19:211-215 (2004) differences described in table 2). CRM197 content in the periplasmic and cytoplasmic fractions were assayed by Elisa.

TABLE 4

| Culture No. | pH before induction | pH during induction | Feed rate during induction (ml/min) | OD650 nm at induction | OD650 nm end of fermentation |
|---|---|---|---|---|---|
| CDT337 | 7.0 | 7.8 | 1.10 | 93.0 | 104.0 |
| CDT338 | 7.0 | 7.8 | 0.28 | 93.0 | 102.4 |
| CDT341 | 7.0 | 8.7 | 0.89 | 94.4 | 40.0 |
| CDT342 | 7.0 | 6.9 | 0.48 | 89.2 | 98.0 |
| CDT344 | 7.0 | 6.9 | 0.89 | 90.0 | 89.0 |
| CDT345 | 7.0 | 8.7 | 0.48 | 92.8 | 42.0 |
| CDT348 | 7.0 | 7.8 | 0.69 | 89.2 | 97.6 |
| CDT349 | 7.0 | 7.8 | 0.69 | 96.0 | 109.0 |
| CDT360 | 7.4 | 8.1 | 0.89 | 88.4 | 98.8 |
| CDT351 | 6.6 | 7.5 | 0.48 | 89.2 | 99.0 |
| CDT354 | 6.6 | 7.5 | 0.89 | 89.0 | 93.6 |
| CDT355 | 6.6 | 8.4 | 0.69 | 87.0 | 40.0 |
| CDT357 | 7.4 | 7.1 | 0.48 | 84.8 | 88.8 |
| CDT358 | 7.4 | 7.2 | 0.69 | 84.0 | 86.4 |
| CDT358 | 7.0 | 7.8 | 0.69 | 94.8 | 108.0 |

TABLE 5

| Culture no. | pH before induction | pH during induction | Feed rate during induction (ml/min) | CRM197 (mg/L by Elisa) Periplasmic | CRM197 (mg/L by Elisa) Cytoplasmic |
|---|---|---|---|---|---|
| CDT337 | 7.0 | 7.8 | 1.10 | 1500 | 422 |
| CDT338 | 7.0 | 7.8 | 0.28 | 921 | 357 |
| CDT341 | 7.0 | 8.7 | 0.89 | 13 | 11 |
| CDT342 | 7.0 | 6.9 | 0.48 | 1058 | 341 |
| CDT344 | 7.0 | 6.9 | 0.89 | 822 | 275 |
| CDT345 | 7.0 | 8.7 | 0.48 | 10 | 20 |
| CDT348 | 7.0 | 7.8 | 0.69 | 1166 | 558 |
| CDT349 | 7.0 | 7.8 | 0.69 | 889 | 652 |
| CDT360 | 7.4 | 8.1 | 0.89 | 77 | 50 |
| CDT351 | 6.6 | 7.5 | 0.48 | 1533 | 427 |
| CDT354 | 6.6 | 7.5 | 0.89 | 803 | 595 |
| CDT355 | 6.6 | 8.4 | 0.69 | 20 | 32 |
| CDT357 | 7.4 | 7.1 | 0.48 | 54 | 29 |
| CDT358 | 7.4 | 7.2 | 0.69 | 681 | 310 |
| CDT359 | 7.0 | 7.8 | 0.69 | 1523 | 685 |

Based on the results from the 15 fermentations, the NEMROD-W software (LPRAI, Marseille, France) was used to model the production of CRM197 in the periplasmic and cytoplasmic fractions.

Figure 2:
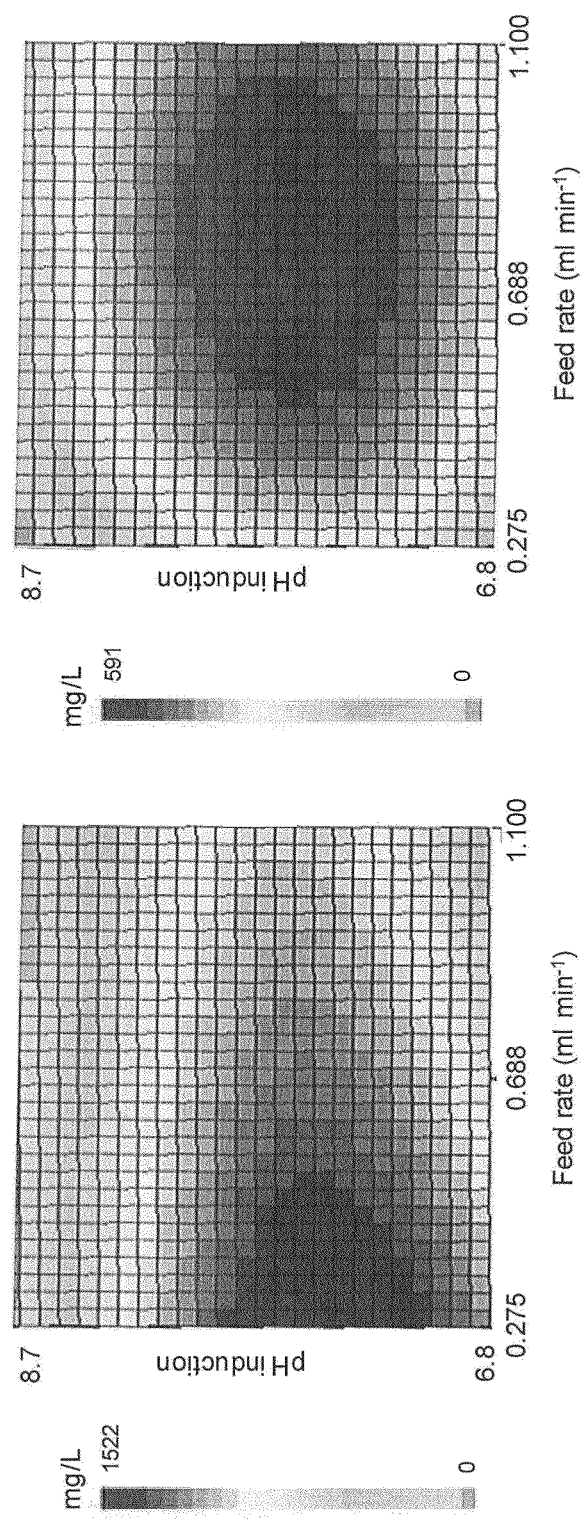
FIG. 2—Depiction of the production of CRM197 in the periplasmic and cell-associated fractions as a function of the feed rate and pH during induction, for growth performed at pH 6.8. The left panel shows periplasmic CRM197 production. The right panel describes cell-associated CRM197 production.

As shown in FIG. 2, the production of periplasmic CRM197 was higher at low feed rates during induction (FIG. 2a), while the accumulation of CRM197 inside the cell was higher at higher feed rates (FIG. 2b). The difference in feed rate optima for the production of periplasmic or cell-associated CRM197 allows for defining conditions that selectively improve the production of periplasmic CRM197. A pH increase at induction is also leads to higher levels of production of periplasmic CRM197 (FIG. 2a).

Example 4

Effect of Cell Paste Freezing on Efficiency of Periplasmic Release by Osmotic Shock Cells of *Escherichia coli* B834(DE3) expressing the flgI CRM197 construct were grown in a fed-batch culture (20 L-scale), and induction of recombinant protein expression and secretion into the periplasmic space were performed as previously described (examples 1-3), although any other method of fermentation using periplasmic expression would be suitable.

Twenty-six hours after IPTG addition, cells were collected by centrifugation (14,000×g, 10 min., +4° C.). Extraction of periplasmic proteins was immediately performed by osmotic shock using a procedure adapted from Chen et al. (Biochem. Eng. J. 19:211-215 (2004) the differences are summarised in Table 6) on fresh cell pellets equivalent to 10 ml fermentation broth. In parallel, cell pellets equivalent to 10 ml broth were stored at −20° C. for 4 days, thawed at room temperature, and subjected to osmotic shock.

TABLE 6

| | Chen | Procedure used in example 4 |
|---|---|---|
| Harvest centrifugation | 10 min. 4° C. 8,000×g | 10 min. 4° C. 14,000×g |
| Cell pellet washes | twice with RO water | none |
| 1st buffer | TrisHCl 33 mM pH 8.0 + EDTA 0.5 mM + sucrose 20% | TrisHCl 30 mM pH 8.0 + EDTA 0.5 mM + sucrose 20% |
| 2nd buffer | RO water | MgSO4 5 mM |
| Vol 1st buffer | 1.6 | 1 |
| Vol 2nd buffer | 1.6 | 1 |
| Incubation 1st buffer | 10 min. 4° C. agitation | 30 min. RT no shaking |
| Incubation 2nd buffer | 10 min. 4° C. agitation | 30 min. RT no shaking |
| Centrifugation 1st buffer | 10 min. 4° C. 8,000×g | 30 min. RT 15,900×g |
| Centrifugation 2nd buffer | 10 min. 4° C. 8,000×g | 30 min. RT 15,900×g |

CRM197 content was determined by Elisa (detection was carried out using rabbit anti-CRM antibody (Pims 20010665) and anti rabbit IgG (Jackson 111-035-003)) in the supernatant and cell-associated fractions after osmotic shock on frozen or fresh cells. Total protein content was determined by Lowry in the same fractions (Table 7).

TABLE 7

Effect of cell-paste freezing on efficiency of periplasmic release by osmotic shock

|  | CRM197 by Elisa (mg/L) | | Efficiency of periplasmic CRM197 release (%)* | Total protein by Lowry (mg/L) | | CRM197:total protein ratio |
|---|---|---|---|---|---|---|
|  | Released | Cell-associated |  | Released | Cell-associated |  |
| Fresh cells | 567 | 2458 | 19% | 3123 | 40332 | 0.18 |
| Frozen cells | 3210 | 250 | 93% | 8798 | 34249 | 0.36 |

*calculated as 100*CRM197$_{supernatant}$/(CRM197$_{supernatant}$ + CRM197$_{cell-asssociated}$)

While only 19% of the total CRM197 was released from fresh cells, 92% was recovered from frozen cells, representing a >5-fold improvement in the total amount of CRM197 released upon osmotic shock. This improvement was accompanied by a higher release of total proteins (2.8-fold), and an increase in the Elisa:total protein ratio (2-fold).

Example 5

Effect of pH Shock Prior to Osmotic Shock on Efficiency of Periplasmic Release from Fresh Cells Cells of *Escherichia coli* B834(DE3) expressing a fusion protein between the signal peptide of FlgI from *E. coli* (19 aa) (SEQ ID NO:24) and the mature part of CRM197 (595 aa) (SEQ ID NO:28) were grown in a fed-batch culture (20 L-scale), and induction of recombinant protein expression and secretion into the periplasmic space were performed as previously described, although any other method of fermentation using periplasmic expression would be suitable.

Twenty-four hours after IPTG addition, cells were collected by centrifugation (14,000×g, 10 min., +4° C.). Extraction of periplasmic proteins was immediately performed by osmotic shock using a procedure adapted from Chen et al. (Biochem. Eng. J. 19:211-215 (2004), differences are described in table 6 above) on fresh cell pellets equivalent to 10 ml fermentation broth. As a control, cell pellets equivalent to 10 ml broth were also stored at −20° C. for 7 days, thawed at room temperature, and subjected to osmotic shock.

In parallel, 100 ml-aliquots from the fermentation were further incubated in 500 ml-shake flasks (23° C., 200 rpm), with or without addition of 600 µl NH$_4$OH 25% or 60 µl H$_3$PO$_4$ 85%. After 2 h incubation, cells were harvested by centrifugation (14,000×g, 10 min., +4° C.) and immediately subjected to osmotic shock.

CRM197 content was determined by Elisa (detection was carried out using rabbit anti-CRM antibody (Pims 20010665) and anti rabbit IgG (Jackson 111-035-003)) in the supernatant fraction after osmotic shock (Table 8).

TABLE 8

Effect of pH shock prior to osmotic shock on efficiency of periplasmic release from fresh cells

|  | Before treatment | | After treatment | | CRM197 by Elisa (mg/L) |
|---|---|---|---|---|---|
|  | OD$_{650\,nm}$ | pH | OD$_{650\,nm}$ | pH | Released |
| Frozen cells - end of fermentation | 116 | 7.50 | N/A* | N/A* | 3441 |
| Fresh cells - end of fermentation | 116 | 7.50 | N/A* | N/A* | 1031 |
| Fresh cells - no pH shock 2 h 23° C. | 116 | 7.52 | 114 | 7.63 | 1211 |
| Fresh cells - NH$_4$OH 2 h 23° C. | 114 | 7.64 | 114 | 7.67 | 1412 |
| Fresh cells - H$_3$PO$_4$ 2 h 23° C. | 116 | 7.08 | 113 | 7.29 | 1740 |

*N/A, not applicable

In the absence of any treatment, periplasmic extraction on fresh cells was only able to extract 30% of the amount extracted from frozen cells. Further incubation of the cells for 2 h at 23° C. resulted in an improvement (1.2-fold vs. untreated fresh cells). When the same treatment was applied after a slight pH up-shift (addition of 600 µl NH$_4$OH 25%), a 1.4-fold improvement was observed. Finally, when the pH was decreased to ~7.1 prior to the 2 h-incubation period, a 1.7-fold improvement was observed compared to untreated fresh cells.

Thus, by adding a maturation step consisting in a pH downshift, followed by a 2 h-incubation period in the absence of any feed addition or pH control, the efficiency of periplasmic release from fresh cells increased 1.7-fold. In terms of total amount of CRM197, these conditions released 51% of the amount extracted from frozen cells. Importantly, this is not due to cell lysis, as indicated by the constant OD$_{650nm}$ during the 2 h-treatment.

Example 6

Effect of the Amplitude of a pH Down-Shift Prior to Osmotic Shock on Efficiency of Periplasmic Release from Fresh Cells Cells of *Escherichia coli* B834(DE3) expressing a fusion protein between the signal peptide of FlgI from *E. coli* (19 as) (SEQ ID NO:24) and the mature part of CRM197 (595 aa) (SEQ ID NO: 28) were grown in a fed-batch culture (150 L-scale), and induction of recombinant protein expression and secretion into the periplasmic space were performed as previously described, although any other method of fermentation using periplasmic expression would be suitable.

Twenty-four hours after IPTG addition, cells were collected by centrifugation (14,000×g, 10 min., +4° C.). Extraction of periplasmic proteins was immediately performed by osmotic shock using a procedure adapted from Chen et al. (Biochem. Eng. J. 19:211-215 (2004) differences described in table 6 above) on fresh cell pellets equivalent to 10 ml fermentation broth. As a control, cell pellets equivalent to 10 ml broth were also stored at −20° C. for 30 days, thawed at room temperature, and subjected to osmotic shock.

In parallel, 100 ml-aliquots from the fermentation were further incubated in 500 ml-shake flasks (23° C., 200 rpm), to which increasing amounts of $H_3PO_4$ 85% were added (0, 60, 120, 180, or 240 µl). After 2 h incubation, cells were harvested by centrifugation (14,000×g, 10 min., +4° C.) and immediately subjected to osmotic shock.

CRM197 content was determined by Elisa (detection was carried out using rabbit anti-CRM antibody (Pims 20010665) and anti rabbit IgG (Jackson 111-035-003)) in the supernatant fraction after osmotic shock (Table 9).

Example 7

Effect of a pH Down-Shift on Efficiency of Periplasmic Release from Fresh Cells at the 20 L-Scale Cells of *Escherichia coli* B834(DE3) expressing a fusion protein between the signal peptide of FlgI from *E. coli* (19 aa) (SEQ ID NO:24) and the mature part of CRM197 (595 aa) (SEQ ID NO:28) were grown in a fed-batch culture (20 L-scale), and induction of recombinant protein expression and secretion into the periplasmic space were performed as previously, although any other method of fermentation using periplasmic expression would be suitable.

Twenty-six hours after IPTG addition, 10 ml-aliquots were collected and centrifuged (14,000×g, 10 min., +4° C.) for extraction of periplasmic proteins by osmotic shock on fresh cells (performed immediately) or frozen cells (cell pellet stored at −20° C. for 4 days), using a procedure adapted from Chen et al. (Biochem. Eng. J. 19:211-215 (2004) differences described in table 6 above).

TABLE 9

Effect of amplitude of pH down-shift prior to osmotic shock on efficiency of periplasmic release from fresh cells

| | Before treatment | | After treatment | | CRM197 by Elisa (mg/L) | | |
|---|---|---|---|---|---|---|---|
| | $OD_{650nm}$ | pH | $OD_{650nm}$ | pH | Released | Cell-associated | Release efficiency** |
| Frozen cells—end of fermentation | 109 | 7.50 | N/A* | N/A* | 2912 | 387 | 88%— |
| Fresh cells—end of fermentation | 109 | 7.50 | N/A* | N/A* | 622 | 1780 | 26%— |
| Fresh cells—0 µl $H_3PO_4$ 2 h 23° C. | 110 | 7.49 | 106 | 7.55 | 1429 | 1532 | 48%— |
| Fresh cells—60 µl $H_3PO_4$ 2 h 23° C. | 113 | 7.14 | 107 | 7.23 | 1677 | 1299 | 56%— |
| Fresh cells—120 µl $H_3PO_4$ 2 h 23° C. | 113 | 6.89 | 105 | 6.96 | 2084 | 1339 | 61%— |
| Fresh cells—180 µl $H_3PO_4$ 2 h 23° C. | 113 | 6.68 | 107 | 6.74 | 1934 | 813 | (70%)*** |
| Fresh cells—240 µl $H_3PO_4$ 2 h 23° C. | 104 | 6.40 | 104 | 6.50 | 2061 | 490 | (81%)*** |

*N/A not applicable
**calculated as 100*$CRM197_{supernatant}$/($CRM197_{supernatant}$ + $CRM197_{cell-associated}$)
***CRM197 degradation observed In the absence of any treatment, periplasmic extraction on fresh cells only extracted 26% of the total CRM197 available, compared to 88% on frozen cells (4.7-fold lower efficiency). Further incubation of the cells for 2 h at 23° C. resulted in a 2-fold improvement in the amount of CRM197 released from fresh cells. This positive effect was enhanced by lowering the pH prior to the 2 h-incubation period. The amount of CRM197 released increased at lower pH. When a pH down-shift to approximately 6.9 was performed, 61% of the total CRM197 available was released from fresh cells (2.7-fold improvement vs. untreated fresh cells). At pH values lower than ~6.9, no further increase in the amount of released CRM197 was observed, while the CRM197 protein was found to be unstable.

Thus, by adding a maturation step consisting in a pH down-shift to 6.9, followed by a 2 h-incubation period in the absence of any feed addition or pH control, the efficiency of periplasmic release from fresh cells could be increased from 21% to 72% of the amount of CRM197 released from untreated frozen cells (calculated as 100*$CRM197_{released\ from\ fresh\ cells}$/$CRM197_{released\ from\ frozen\ cells}$).

In parallel, 34 g $H_3PO_4$ 85% were added to the fermentation broth in order to lower the pH from 7.5 to 6.8, and feed addition was stopped. All other parameters were kept at their previous set-points. The fermentation was then pursued for 2 h at pH 6.8. During this maturation period, minimal stirring speed was maintained at 300 rpm, which resulted in increasing dissolved oxygen levels (consequence of the low oxygen demand as a result of the absence of feed addition). The fermentation profile during the 2 h incubation period at pH 6.8 is shown in FIG. 3.

After the 2 h-maturation phase, 10 ml-aliquots were collected and centrifuged (14,000×g, 10 min., +4° C.) for extraction of periplasmic proteins by osmotic shock on fresh cells (performed immediately) or frozen cells (cell pellet stored at −20° C. for 4 days).

CRM197 content was determined by Elisa (detection was carried out using rabbit anti-CRM antibody (Pims 20010665) and anti rabbit IgG (Jackson 111-035-003)) in the supernatant and cell-associated fractions after osmotic shock on frozen or fresh cells. Total protein content was determined by Lowry in the same fractions (Table 10).

TABLE 10

Effect of pH down-shift prior to osmotic shock on efficiency of periplasmic release from fresh cells

| | CRM197 by Elisa (m/L) | | | Total protein by Lowry (mg/L) | | |
|---|---|---|---|---|---|---|
| | Released | Cell-associated | CRM197 release (%)* | Released | Cell-associated | CRM197:total protein ratio |
| Fresh cells—no treatment | 567 | 2458 | 19% | 3123 | 40332 | 0.18 |
| Frozen cells—no treatment | 3210 | 250 | 93% | 8798 | 34249 | 0.36 |
| Fresh cells—2 h acidic treatment | 1614 | 1672 | 49% | 4922 | 38774 | 0.33 |
| Frozen cells—2 h acidic treatment | 2809 | 215 | 93% | 7153 | 34027 | 0.39 |

*calculated as $100*CRM197_{supernatant}/(CRM197_{supernatant} + CRM197_{cell\text{-}associated})$ In the absence of acidic treatment, CRM197 release by osmotic shock was 5.7-fold less efficient on fresh cells compared to frozen cells. The 2 h-acidic treatment improved the efficiency of osmotic shock on fresh cells: after the maturation step, 49% of the total CRM197 could be extracted from fresh cells, compared to only 19% in the absence of maturation. This improvement was accompanied by a higher release of total proteins, and an increase in the Elisa:total protein ratio.

Thus, by adding a maturation step consisting in a pH down-shift to 6.8, followed by a 2 h-incubation period in the absence of any feed addition, the efficiency of periplasmic release from fresh cells could be increased from 18% to 50% of the amount of CRM197 released from untreated frozen cells (calculated as $100*CRM197_{released\ from\ fresh\ cells}/CRM197_{released\ from\ frozen\ cells}$).

---

We claim:

1. A process for periplasmic expression of a bacterial toxoid comprising the steps of:
   (a) growing a culture of a gram negative host cell in a fermentation medium, wherein the host cell is selected from the group consisting of *E. Coli, Pseudomonas* and *Moraxella*, and is transformed with a polynucleotide, and wherein the polynucleotide encodes a bacterial toxoid and a periplasmic signal sequence;
   (a(i)) inducing expression of the bacterial toxoid and collecting the host cells from the culture by centrifugation; and then
   (b) maturing the host cells, wherein the maturing step comprises:
      I) subjecting the host cells to a pH shock; and
      II) incubating the host cells in a fermentation medium with no feed addition for at least two hours;
   (c) harvesting the host cells using centrifugation; and
   (d) extracting the bacterial toxoid from the host cells wherein the extraction process comprises osmotic shock;
   wherein the host cells are alive during step (b) and wherein the process is carried out in a fermentor which contains 10-5000 liters of culture.

2. The process of claim 1 wherein the pH shock comprises increasing or decreasing the pH of the fermentation medium by between 0.1 and 2.0 pH units.

3. The process of claim 1 wherein the bacterial toxoid is a diphtheria toxoid.

4. The process of claim 1 wherein the periplasmic signal sequence is selected from the group:
   a) any one of SEQ ID NO: 2, 4, 6, 8, 10, 12, 14, 18, 20, 22, 24, or 26;
   b) a variant of SEQ ID NO:2, 4, 6, 8, 10, 12, 14, 18, 20, 22, 24, or 26 containing 1, 2, or 3 point mutations, insertions or deletions; or
   c) a fragment of at least 10 amino acids of SEQ ID NO: 2, 4, 6, 8, 10, 12, 14, 18, 20, 22, 24, or 26.

5. The process of claim 1, further comprising a step (e) of purifying the bacterial toxoid.

6. The process of claim 5, further comprising conjugating the purified bacterial toxoid to a saccharide, polysaccharide or oligosaccharide.

7. The process of claim 5, further comprising mixing the purified bacterial toxoid with at least one additional antigen.

8. A process for periplasmic expression of a bacterial toxoid comprising the steps of:
   (a) providing a culture of a gram negative host cell selected from the group consisting of *E. coli, Pseudomonas*, and *Moraxella*, wherein the host cell is transformed with a polynucleotide, the polynucleotide encodes a bacterial toxoid and a periplasmic signal sequence, and wherein the gram negative host cell comprises the bacterial toxoid expressed in the periplasm;
   (a)(i) collecting the host cells from the culture by centrifugation;
   (b) maturing the host cell, wherein the maturing step comprises:
      I) subjecting the host cell to a pH shock; and
      II) incubating the host cell in a fermentation medium with no feed addition for at least two hours; and then
   (c) harvesting the host cells using centrifugation; and
   (d) extracting the bacterial toxoid from the host cells, wherein the extraction process comprises osmotic shock;
   wherein the host cells are alive during step (b) and wherein the process is carried out in a fermentor which contains 10-5000 liters of culture.

9. The process of claim 8, wherein the pH shock comprises increasing or decreasing the pH of the fermentation medium by between 0.1 and 2.0 pH units.

10. The process of claim 8, wherein the periplasmic signal sequence is selected from the group of:

a) any one of SEQ ID NO: 2, 4, 6, 8, 10, 12, 14, 18, 20, 22, 24, or 26;
b) a variant of SEQ ID NO:2, 4, 6, 8, 10, 12, 14, 18, 20, 22, 24, or 26 containing 1, 2, or 3 point mutations, insertions or deletions; or
c) a fragment of at least 10 amino acids of SEQ ID NO: 2, 4, 6, 8, 10, 12, 14, 18, 20, 22, 24, or 26.

11. The process of claim 8 further comprising a step (e) of purifying the bacterial toxoid.

12. The process of claim 11, further comprising conjugating the purified bacterial toxoid to a saccharide, polysaccharide or oligosaccharide.

13. The process of claim 11, further comprising mixing the purified bacterial toxoid with at least one additional antigen.

14. The process of claim 8 wherein the bacterial toxoid is a diphtheria toxoid.

15. The process of claim 1 wherein the bacterial toxoid is CRM197.

16. The process of claim 8 wherein the bacterial toxoid is CRM197.

* * * * *

SEQUENCE LISTING

```
<160> NUMBER OF SEQ ID NOS: 28

<210> SEQ ID NO 1
<211> LENGTH: 72
<212> TYPE: DNA
<213> ORGANISM: Artificial Sequence
<220> FEATURE:
<223> OTHER INFORMATION: Nucleotide sequence of the PhtE signal sequence

<400> SEQUENCE: 1
atgaaattta gtaaaaaata tatagcagct ggatcagctg ttatcgtatc cttgagtcta      60
tgtgcctatg ca                                                          72

<210> SEQ ID NO 2
<211> LENGTH: 24
<212> TYPE: PRT
<213> ORGANISM: Artificial Sequence
<220> FEATURE:
<223> OTHER INFORMATION: Amino acid sequence of the PhtE signal sequence

<400> SEQUENCE: 2

Met Lys Phe Ser Lys Lys Tyr Ile Ala Ala Gly Ser Ala Val Ile Val
  1               5                  10                  15

Ser Leu Ser Leu Cys Ala Tyr Ala
            20

<210> SEQ ID NO 3
<211> LENGTH: 75
<212> TYPE: DNA
<213> ORGANISM: Artificial Sequence
<220> FEATURE:
<223> OTHER INFORMATION: Nucleotide sequence of the SipA signal sequence

<400> SEQUENCE: 3
```

```
atgaaaatga ataaaaaggt actattgaca tcgacaatgg cagcttcgct attatcagtc    60
gcaagtgttc aagca                                                     75
```

<210> SEQ ID NO 4
<211> LENGTH: 25
<212> TYPE: PRT
<213> ORGANISM: Artificial Sequence
<220> FEATURE:
<223> OTHER INFORMATION: Amino acid sequence of the SipA signal sequence

<400> SEQUENCE: 4

```
Met Lys Met Asn Lys Lys Val Leu Leu Thr Ser Thr Met Ala Ala Ser
  1               5                  10                  15

Leu Leu Ser Val Ala Ser Val Gln Ala
            20                  25
```

<210> SEQ ID NO 5
<211> LENGTH: 63
<212> TYPE: DNA
<213> ORGANISM: Artificial Sequence
<220> FEATURE:
<223> OTHER INFORMATION: Nucleotide sequence of the OmpA signal sequence

<400> SEQUENCE: 5

```
atgaaaaaga cagctatcgc gattgcagtg gcactggctg gtttcgctac cgtagcgcag    60
gcc                                                                  63
```

<210> SEQ ID NO 6
<211> LENGTH: 21
<212> TYPE: PRT
<213> ORGANISM: Artificial Sequence
<220> FEATURE:
<223> OTHER INFORMATION: Amino acid sequence of the OmpA signal sequence

<400> SEQUENCE: 6

```
Met Lys Lys Thr Ala Ile Ala Ile Ala Val Ala Leu Ala Gly Phe Ala
  1               5                  10                  15

Thr Val Ala Gln Ala
            20
```

<210> SEQ ID NO 7
<211> LENGTH: 57
<212> TYPE: DNA
<213> ORGANISM: Artificial Sequence
<220> FEATURE:
<223> OTHER INFORMATION: Nucleotide sequence of the NspA signal sequence

<400> SEQUENCE: 7

```
atgaaaaaag cacttgccac actgattgcc ctcgctctcc cggccgccgc actggcg       57
```

<210> SEQ ID NO 8
<211> LENGTH: 19
<212> TYPE: PRT
<213> ORGANISM: Artificial Sequence
<220> FEATURE:
<223> OTHER INFORMATION: Amino acid sequence of the NspA signal sequence

<400> SEQUENCE: 8

```
Met Lys Lys Ala Leu Ala Thr Leu Ile Ala Leu Ala Leu Pro Ala Ala
  1               5                  10                  15

Ala Leu Ala
```

<210> SEQ ID NO 9

```
<211> LENGTH: 54
<212> TYPE: DNA
<213> ORGANISM: Artificial Sequence
<220> FEATURE:
<223> OTHER INFORMATION: Nucleotide sequence of the TorT signal sequence

<400> SEQUENCE: 9
atgcgcgtac tgctattttt acttctttcc cttttcatgt tgccggcatt ttcg          54

<210> SEQ ID NO 10
<211> LENGTH: 18
<212> TYPE: PRT
<213> ORGANISM: Artificial Sequence
<220> FEATURE:
<223> OTHER INFORMATION: Amino acid sequence of the TorT signal sequence

<400> SEQUENCE: 10

Met Arg Val Leu Leu Phe Leu Leu Leu Ser Leu Phe Met Leu Pro Ala
  1               5                  10                  15

Phe Ser

<210> SEQ ID NO 11
<211> LENGTH: 69
<212> TYPE: DNA
<213> ORGANISM: Artificial Sequence
<220> FEATURE:
<223> OTHER INFORMATION: Nucleotide sequence of the SfmC signal sequence

<400> SEQUENCE: 11
atgatgacta aaataaagtt attgatgctc attatatttt atttaatcat ttcggccagc    60
gcccatgct                                                           69

<210> SEQ ID NO 12
<211> LENGTH: 23
<212> TYPE: PRT
<213> ORGANISM: Artificial Sequence
<220> FEATURE:
<223> OTHER INFORMATION: Amino acid sequence of the SfmC signal sequence

<400> SEQUENCE: 12

Met Met Thr Lys Ile Lys Leu Leu Met Leu Ile Ile Phe Tyr Leu Ile
  1               5                  10                  15

Ile Ser Ala Ser Ala His Ala
                 20

<210> SEQ ID NO 13
<211> LENGTH: 75
<212> TYPE: DNA
<213> ORGANISM: Artificial Sequence
<220> FEATURE:
<223> OTHER INFORMATION: Nucleotide sequence of the FocC signal sequence

<400> SEQUENCE: 13
atgatgaagc acatgcgtat atgggccgtt ctggcatcat ttttagtctt tttttatatt    60
ccgcagagct atgcc                                                    75

<210> SEQ ID NO 14
<211> LENGTH: 25
<212> TYPE: PRT
<213> ORGANISM: Artificial Sequence
<220> FEATURE:
<223> OTHER INFORMATION: Amino acid sequence of the FocC signal sequence

<400> SEQUENCE: 14
```

Met Met Lys His Met Arg Ile Trp Ala Val Leu Ala Ser Phe Leu Val
1               5                   10                  15

Phe Phe Tyr Ile Pro Gln Ser Tyr Ala
            20                  25

<210> SEQ ID NO 15
<211> LENGTH: 54
<212> TYPE: DNA
<213> ORGANISM: Artificial Sequence
<220> FEATURE:
<223> OTHER INFORMATION: Nucleotide sequence of the CcmH signal sequence

<400> SEQUENCE: 15
atgaggtttt tattgggcgt gctgatgctg atgatctccg gctcagcgct ggcg        54

<210> SEQ ID NO 16
<211> LENGTH: 18
<212> TYPE: PRT
<213> ORGANISM: Artificial Sequence
<220> FEATURE:
<223> OTHER INFORMATION: Amino acid sequence of the CcmH signal sequence

<400> SEQUENCE: 16

Met Arg Phe Leu Leu Gly Val Leu Met Leu Met Ile Ser Gly Ser Ala
1               5                   10                  15

Leu Ala

<210> SEQ ID NO 17
<211> LENGTH: 69
<212> TYPE: DNA
<213> ORGANISM: Artificial Sequence
<220> FEATURE:
<223> OTHER INFORMATION: Nucleotide sequence of the YraI signal sequence

<400> SEQUENCE: 17
atgtcaaaac gaacattcgc ggtgatatta accttgttgt gtagcttctg tattggccag    60
gcgcttgca                                                            69

<210> SEQ ID NO 18
<211> LENGTH: 23
<212> TYPE: PRT
<213> ORGANISM: Artificial Sequence
<220> FEATURE:
<223> OTHER INFORMATION: Amino acid sequence of the YraI signal sequence

<400> SEQUENCE: 18

Met Ser Lys Arg Thr Phe Ala Val Ile Leu Thr Leu Leu Cys Ser Phe
1               5                   10                  15

Cys Ile Gly Gln Ala Leu Ala
            20

<210> SEQ ID NO 19
<211> LENGTH: 66
<212> TYPE: DNA
<213> ORGANISM: Artificial Sequence
<220> FEATURE:
<223> OTHER INFORMATION: Nucleotide sequence of the TolB signal sequence

<400> SEQUENCE: 19
atgatgaagc aggcattacg agtagcattt ggttttctca tactgtgggc atcagttctg    60
catgct                                                               66

<210> SEQ ID NO 20

-continued

<210> SEQ ID NO 20
<211> LENGTH: 22
<212> TYPE: PRT
<213> ORGANISM: Artificial Sequence
<220> FEATURE:
<223> OTHER INFORMATION: Amino acid sequence of the TolB signal sequence

<400> SEQUENCE: 20

Met Met Lys Gln Ala Leu Arg Val Ala Phe Gly Phe Leu Ile Leu Trp
1               5                   10                  15

Ala Ser Val Leu His Ala
            20

<210> SEQ ID NO 21
<211> LENGTH: 66
<212> TYPE: DNA
<213> ORGANISM: Artificial Sequence
<220> FEATURE:
<223> OTHER INFORMATION: nucleotide sequence of the NikA signal sequence

<400> SEQUENCE: 21
atgctctcca cactccgccg cactctattt gcgctgctgg cttgtgcgtc ttttatcgtc      60
catgcc                                                                66

<210> SEQ ID NO 22
<211> LENGTH: 22
<212> TYPE: PRT
<213> ORGANISM: Artificial Sequence
<220> FEATURE:
<223> OTHER INFORMATION: Amino acid sequence of the NikA signal sequence

<400> SEQUENCE: 22

Met Leu Ser Thr Leu Arg Arg Thr Leu Phe Ala Leu Leu Ala Cys Ala
1               5                   10                  15

Ser Phe Ile Val His Ala
            20

<210> SEQ ID NO 23
<211> LENGTH: 57
<212> TYPE: DNA
<213> ORGANISM: Artificial Sequence
<220> FEATURE:
<223> OTHER INFORMATION: Nucleotide sequence of the FlgI signal sequence

<400> SEQUENCE: 23
atgattaaat ttctctctgc attaattctt ctactggtca cgacggcggc tcaggct         57

<210> SEQ ID NO 24
<211> LENGTH: 19
<212> TYPE: PRT
<213> ORGANISM: Artificial Sequence
<220> FEATURE:
<223> OTHER INFORMATION: Amino acid sequence of the FlgI signal sequence

<400> SEQUENCE: 24

Met Ile Lys Phe Leu Ser Ala Leu Ile Leu Leu Leu Val Thr Thr Ala
1               5                   10                  15

Ala Gln Ala

<210> SEQ ID NO 25
<211> LENGTH: 57
<212> TYPE: DNA
<213> ORGANISM: Artificial Sequence
<220> FEATURE:
<223> OTHER INFORMATION: Nucleotide sequence of the DsbA signal sequence

<400> SEQUENCE: 25

```
atgaaaaaga tttggctggc gctggctggt ttagttttag cgtttagcgc atcggcg      57
```

<210> SEQ ID NO 26
<211> LENGTH: 19
<212> TYPE: PRT
<213> ORGANISM: Artificial Sequence
<220> FEATURE:
<223> OTHER INFORMATION: Amino acid sequence of the DsbA signal sequence

<400> SEQUENCE: 26

```
Met Lys Lys Ile Trp Leu Ala Leu Ala Gly Leu Val Leu Ala Phe Ser
  1               5                  10                  15

Ala Ser Ala
```

<210> SEQ ID NO 27
<211> LENGTH: 1605
<212> TYPE: DNA
<213> ORGANISM: Corynebacterium diphtheriae

<400> SEQUENCE: 27
ggtgcggatg atgtggtgga tagcagcaaa tcttttgtga tggaaaactt tagcagctat 60
catggcacca aaccgggcta tgtggatagc attcagaaag gcatccagaa accgaaaagc 120
ggcacccagg gcaactatga tgatgattgg aaagaatttt atagcaccga taacaaatat 180
gatgcggcgg gttatagcgt ggataacgaa aatccgctgt ctggcaaagc gggcggtgtg 240
gtgaaagtga cctatccggg cctgaccaaa gtgctggccc tgaaagtgga taacgcggaa 300
accatcaaaa aagaactggg cctgagcctg accgaaccgc tgatggaaca ggtgggcacc 360
gaagaattta ttaaacgctt tggcgatggc gcgagccgtg tggttctgag cctgccgttt 420
gcggaaggca gcagcagcgt ggaatatatt aacaactggg aacaggcgaa agccctgagc 480
gtggaactgg aaattaactt tgaaacccgt ggcaaacgtg gccaggatgc gatgtatgaa 540
tacatggcgc aggcgtgcgc gggcaatcgt gtgcgtcgta gcgtgggcag cagcctgagc 600
tgcattaacc tggattggga cgtcattcgt gataaaacca aaaccaaaat cgaaagcctg 660
aaagaacatg gcccgatcaa aaacaaaatg agcgaaagcc cgaacaaaac cgtgagcgaa 720
gaaaaagcga aacagtatct ggaagaattt catcagaccg cgctggaaca tccggaactg 780
agcgaactga aaaccgtgac cggcaccaat ccggtgtttg cgggtgcgaa ctatgcggcg 840
tgggcggtga atgtggcgca ggtgattgat agcgaaaccg cggataacct ggaaaaaacc 900
accgcggccc tgagcattct gccgggcatt ggcagcgtga tgggcattgc ggatggcgcg 960
gtgcatcata acaccgaaga aattgtggcg cagagcattg ccctgagcag cctgatggtg 1020
gcgcaggcga ttccgctggt tggcgaactg gtggatattg gctttgcggc gtacaacttt 1080
gtggaaagca tcatcaacct gtttcaggtg gtgcataaca gctataaccg tccggcgtat 1140
tctccgggtc ataaaaccca gccgtttctg catgatggct atgcggtgag ctggaacacc 1200
gtggaagata gcattattcg taccggcttt cagggcgaaa gcggccatga tattaaaatt 1260
accgcggaaa acaccccgct gccgattgcg ggtgttctgc tgccgaccat tccgggcaaa 1320
ctggatgtga acaaaagcaa aacccatatt agcgtgaacg gtcgtaaaat tcgtatgcgt 1380
tgccgtgcga ttgatggcga tgtgaccttt tgccgtccga aagcccggt gtatgtgggc 1440 aacggcgtgc acgcgaacct gcatgtggcg tttcatcgta gcagcagcga aaaaatccat 1500
agcaacgaaa ttagcagcga tagcattggc gtgctgggct atcagaaaac cgtggaccat 1560

```
accaaagtga actctaaact gagcctgttc ttcgaaatca aaagc                                1605
```

<210> SEQ ID NO 28
<211> LENGTH: 535
<212> TYPE: PRT
<213> ORGANISM: Corynebacterium diphtheriae

<400> SEQUENCE: 28

| Gly | Ala | Asp | Asp | Val | Val | Asp | Ser | Ser | Lys | Ser | Phe | Val | Met | Glu | Asn |
|---|---|---|---|---|---|---|---|---|---|---|---|---|---|---|---|
| 1 | | | | 5 | | | | | 10 | | | | | 15 | |

| Phe | Ser | Ser | Tyr | His | Gly | Thr | Lys | Pro | Gly | Tyr | Val | Asp | Ser | Ile | Gln |
|---|---|---|---|---|---|---|---|---|---|---|---|---|---|---|---|
| | | | 20 | | | | | 25 | | | | | 30 | | |

| Lys | Gly | Ile | Gln | Lys | Pro | Lys | Ser | Gly | Thr | Gln | Gly | Asn | Tyr | Asp | Asp |
|---|---|---|---|---|---|---|---|---|---|---|---|---|---|---|---|
| | | 35 | | | | | 40 | | | | | 45 | | | |

| Asp | Trp | Lys | Glu | Phe | Tyr | Ser | Thr | Asp | Asn | Lys | Tyr | Asp | Ala | Ala | Gly |
|---|---|---|---|---|---|---|---|---|---|---|---|---|---|---|---|
| | 50 | | | | | 55 | | | | | 60 | | | | |

| Tyr | Ser | Val | Asp | Asn | Glu | Asn | Pro | Leu | Ser | Gly | Lys | Ala | Gly | Gly | Val |
|---|---|---|---|---|---|---|---|---|---|---|---|---|---|---|---|
| 65 | | | | | 70 | | | | | 75 | | | | | 80 |

| Val | Lys | Val | Thr | Tyr | Pro | Gly | Leu | Thr | Lys | Val | Leu | Ala | Leu | Lys | Val |
|---|---|---|---|---|---|---|---|---|---|---|---|---|---|---|---|
| | | | | 85 | | | | | 90 | | | | | 95 | |

| Asp | Asn | Ala | Glu | Thr | Ile | Lys | Lys | Glu | Leu | Gly | Leu | Ser | Leu | Thr | Glu |
|---|---|---|---|---|---|---|---|---|---|---|---|---|---|---|---|
| | | | | 100 | | | | | 105 | | | | | 110 | |

| Pro | Leu | Met | Glu | Gln | Val | Gly | Thr | Glu | Glu | Phe | Ile | Lys | Arg | Phe | Gly |
|---|---|---|---|---|---|---|---|---|---|---|---|---|---|---|---|
| | | 115 | | | | | 120 | | | | | 125 | | | |

| Asp | Gly | Ala | Ser | Arg | Val | Val | Leu | Ser | Leu | Pro | Phe | Ala | Glu | Gly | Ser |
|---|---|---|---|---|---|---|---|---|---|---|---|---|---|---|---|
| | 130 | | | | | 135 | | | | | 140 | | | | |

| Ser | Ser | Val | Glu | Tyr | Ile | Asn | Asn | Trp | Glu | Gln | Ala | Lys | Ala | Leu | Ser |
|---|---|---|---|---|---|---|---|---|---|---|---|---|---|---|---|
| 145 | | | | | 150 | | | | | 155 | | | | | 160 |

| Val | Glu | Leu | Glu | Ile | Asn | Phe | Glu | Thr | Arg | Gly | Lys | Arg | Gly | Gln | Asp |
|---|---|---|---|---|---|---|---|---|---|---|---|---|---|---|---|
| | | | | 165 | | | | | 170 | | | | | 175 | |

| Ala | Met | Tyr | Glu | Tyr | Met | Ala | Gln | Ala | Cys | Ala | Gly | Asn | Arg | Val | Arg |
|---|---|---|---|---|---|---|---|---|---|---|---|---|---|---|---|
| | | | 180 | | | | | 185 | | | | | 190 | | |

| Arg | Ser | Val | Gly | Ser | Ser | Leu | Ser | Cys | Ile | Asn | Leu | Asp | Trp | Asp | Val |
|---|---|---|---|---|---|---|---|---|---|---|---|---|---|---|---|
| | | 195 | | | | | 200 | | | | | 205 | | | |

| Ile | Arg | Asp | Lys | Thr | Lys | Thr | Lys | Ile | Glu | Ser | Leu | Lys | Glu | His | Gly |
|---|---|---|---|---|---|---|---|---|---|---|---|---|---|---|---|
| | 210 | | | | | 215 | | | | | 220 | | | | |

| Pro | Ile | Lys | Asn | Lys | Met | Ser | Glu | Ser | Pro | Asn | Lys | Thr | Val | Ser | Glu |
|---|---|---|---|---|---|---|---|---|---|---|---|---|---|---|---|
| 225 | | | | | 230 | | | | | 235 | | | | | 240 |

| Glu | Lys | Ala | Lys | Gln | Tyr | Leu | Glu | Glu | Phe | His | Gln | Thr | Ala | Leu | Glu |
|---|---|---|---|---|---|---|---|---|---|---|---|---|---|---|---|
| | | | | 245 | | | | | 250 | | | | | 255 | |

| His | Pro | Glu | Leu | Ser | Glu | Leu | Lys | Thr | Val | Thr | Gly | Thr | Asn | Pro | Val |
|---|---|---|---|---|---|---|---|---|---|---|---|---|---|---|---|
| | | | 260 | | | | | 265 | | | | | 270 | | |

| Phe | Ala | Gly | Ala | Asn | Tyr | Ala | Ala | Trp | Ala | Val | Asn | Val | Ala | Gln | Val |
|---|---|---|---|---|---|---|---|---|---|---|---|---|---|---|---|
| | 275 | | | | | 280 | | | | | 285 | | | | |

| Ile | Asp | Ser | Glu | Thr | Ala | Asp | Asn | Leu | Glu | Lys | Thr | Thr | Ala | Ala | Leu |
|---|---|---|---|---|---|---|---|---|---|---|---|---|---|---|---|
| 290 | | | | | 295 | | | | | 300 | | | | | |

| Ser | Ile | Leu | Pro | Gly | Ile | Gly | Ser | Val | Met | Gly | Ile | Ala | Asp | Gly | Ala |
|---|---|---|---|---|---|---|---|---|---|---|---|---|---|---|---|
| 305 | | | | | 310 | | | | | 315 | | | | | 320 |

| Val | His | His | Asn | Thr | Glu | Glu | Ile | Val | Ala | Gln | Ser | Ile | Ala | Leu | Ser |
|---|---|---|---|---|---|---|---|---|---|---|---|---|---|---|---|
| | | | | 325 | | | | | 330 | | | | | 335 | |

| Ser | Leu | Met | Val | Ala | Gln | Ala | Ile | Pro | Leu | Val | Gly | Glu | Leu | Val | Asp |
|---|---|---|---|---|---|---|---|---|---|---|---|---|---|---|---|
| | | | 340 | | | | | 345 | | | | | 350 | | |

| Ile | Gly | Phe | Ala | Ala | Tyr | Asn | Phe | Val | Glu | Ser | Ile | Ile | Asn | Leu | Phe |
|---|---|---|---|---|---|---|---|---|---|---|---|---|---|---|---|
| | | 355 | | | | | 360 | | | | | 365 | | | |

-continued

```
Gln Val Val His Asn Ser Tyr Asn Arg Pro Ala Tyr Ser Pro Gly His
    370             375             380
Lys Thr Gln Pro Phe Leu His Asp Gly Tyr Ala Val Ser Trp Asn Thr
385             390             395                 400
Val Glu Asp Ser Ile Ile Arg Thr Gly Phe Gln Gly Glu Ser Gly His
            405             410             415
Asp Ile Lys Ile Thr Ala Glu Asn Thr Pro Leu Pro Ile Ala Gly Val
            420             425             430
Leu Leu Pro Thr Ile Pro Gly Lys Leu Asp Val Asn Lys Ser Lys Thr
        435             440             445
His Ile Ser Val Asn Gly Arg Lys Ile Arg Met Arg Cys Arg Ala Ile
    450             455             460
Asp Gly Asp Val Thr Phe Cys Arg Pro Lys Ser Pro Val Tyr Val Gly
465             470             475             480
Asn Gly Val His Ala Asn Leu His Val Ala Phe His Arg Ser Ser Ser
            485             490             495
Glu Lys Ile His Ser Asn Glu Ile Ser Ser Asp Ser Ile Gly Val Leu
            500             505             510
Gly Tyr Gln Lys Thr Val Asp His Thr Lys Val Asn Ser Lys Leu Ser
        515             520             525
Leu Phe Phe Glu Ile Lys Ser
        530             535
```